(12) United States Patent
Swager et al.

(10) Patent No.: US 12,277,464 B2
(45) Date of Patent: **\*Apr. 15, 2025**

(54) SYSTEM FOR DETECTING A STIMULUS INCLUDING A RADIO FREQUENCY DEVICE RESPONSIVE TO AN ANALYTE AND A PORTABLE READER

(71) Applicant: Massachusetts Institute of Technology, Cambridge, MA (US)

(72) Inventors: Timothy Manning Swager, Newton, MA (US); Joseph Michael Azzarelli, Cambridge, MA (US); Rong Zhu, Waltham, MA (US)

(73) Assignee: Massachusetts Institute of Technology, Cambridge, MA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 17/539,803

(22) Filed: Dec. 1, 2021

(65) Prior Publication Data
US 2022/0343126 A1 Oct. 27, 2022

Related U.S. Application Data

(63) Continuation of application No. 16/732,095, filed on Dec. 31, 2019, now Pat. No. 11,200,474, which is a
(Continued)

(51) Int. Cl.
*G06K 19/07* (2006.01)
*A61B 5/00* (2006.01)
(Continued)

(52) U.S. Cl.
CPC .......... *G06K 19/0717* (2013.01); *A61B 5/082* (2013.01); *A61B 5/4845* (2013.01);
(Continued)

(58) Field of Classification Search
CPC .......... G06K 19/0716; G06K 19/0717; G01N 27/121; G01N 27/4146; G01N 2033/0093; A61B 5/082; A61B 2562/029
(Continued)

(56) References Cited

U.S. PATENT DOCUMENTS 5,571,401 A  11/1996  Lewis et al.
6,783,989 B1  8/2004  Zakin
(Continued)

FOREIGN PATENT DOCUMENTS

CN  103435849 A  12/2013

OTHER PUBLICATIONS

International Search Report and Written Opinion mailed Nov. 3, 2017, for Application No. PCT/US2017/038043.
(Continued)

*Primary Examiner* — Suezu Ellis
(74) *Attorney, Agent, or Firm* — Wolf, Greenfield & Sacks, P.C.

(57) ABSTRACT

A wireless sensor platform design and a single walled carbon nanotube/ionic liquid-based chemidosimeter system can incorporated into a highly sensitive and selective chemical hazard badge that can dosimetrically detect an analyte down to a sub parts-per-million concentration.

18 Claims, 23 Drawing Sheets

Related U.S. Application Data continuation of application No. 15/626,041, filed on Jun. 16, 2017, now abandoned.

(60) Provisional application No. 62/351,881, filed on Jun. 17, 2016.

(51) Int. Cl.
| | | |
|---|---|---|
| *A61B 5/08* | (2006.01) | |
| *G01N 27/12* | (2006.01) | |
| *G01N 27/414* | (2006.01) | |
| *G01N 33/00* | (2006.01) | |
| *G06Q 50/26* | (2012.01) | |

(52) U.S. Cl.
CPC ....... *G01N 27/122* (2013.01); *G01N 27/4146* (2013.01); *G01N 33/0075* (2013.01); *G06Q 50/265* (2013.01); *A61B 2562/0285* (2013.01); *A61B 2562/029* (2013.01); *G01N 27/127* (2013.01); *G01N 33/0057* (2013.01)

(58) Field of Classification Search
USPC ........ 235/451, 492; 340/572.1, 572.2, 572.5, 340/539.26, 539.2
See application file for complete search history.

(56) References Cited

U.S. PATENT DOCUMENTS

| | | | |
|---|---|---|---|
| 8,159,347 | B2 | 4/2012 | Potyrailo et al. |
| 9,563,833 | B2 | 2/2017 | Swager et al. |
| 11,200,474 | B2* | 12/2021 | Swager ................ G01N 27/122 |
| 2009/0278685 | A1* | 11/2009 | Potyrailo ............ G01N 33/0006 340/572.1 |
| 2010/0022010 | A1 | 1/2010 | Stevens et al. |
| 2010/0073135 | A1 | 3/2010 | Potyrailo et al. |
| 2011/0089051 | A1 | 4/2011 | Wang et al. |
| 2011/0267077 | A1 | 11/2011 | Dimmler et al. |
| 2012/0183949 | A1 | 7/2012 | Hyde et al. |
| 2013/0230429 | A1* | 9/2013 | Naishadham ...... G01N 29/2481 422/83 |
| 2015/0116093 | A1* | 4/2015 | Swager ............ G06K 19/0723 340/10.4 |
| 2016/0008182 | A1 | 1/2016 | Prokopuk et al. |
| 2017/0023509 | A1 | 1/2017 | Kim et al. |
| 2017/0212104 | A1 | 7/2017 | Schnorr et al. |

OTHER PUBLICATIONS

Cook et al., RFID-based sensors for zero-power autonomous wireless sensor networks. IEEE Sensors Journal. Jan. 2014; 14(8): 2419-31.

Liu et al., Chemical-vapor-sensitive materials based on a multiwalled carbon nanotube/hydroxyl propyl methylcellulose/cellulose composite. J Appl Polymer Sci. Nov. 22, 2017; 132(11): 41639.

Wang et al., Diverse chemiresistors based upon covalently modified multiwalled carbon nanotubes. J Am Chem Soc. Jul. 27, 2011;133(29):11181-93. doi: 10.1021/ja201860g. Epub Jun. 30, 2011.

Zhou et al., A Fluorescent Sensor for Dual-Channel Discrimination between Phosgene and a Nerve-Gas Mimic. Angew Chem Int Ed Engl. Apr. 4, 2016;55(15):4729-33. doi: 10.1002/anie.201601346. Epub Mar. 3, 2016.

* cited by examiner

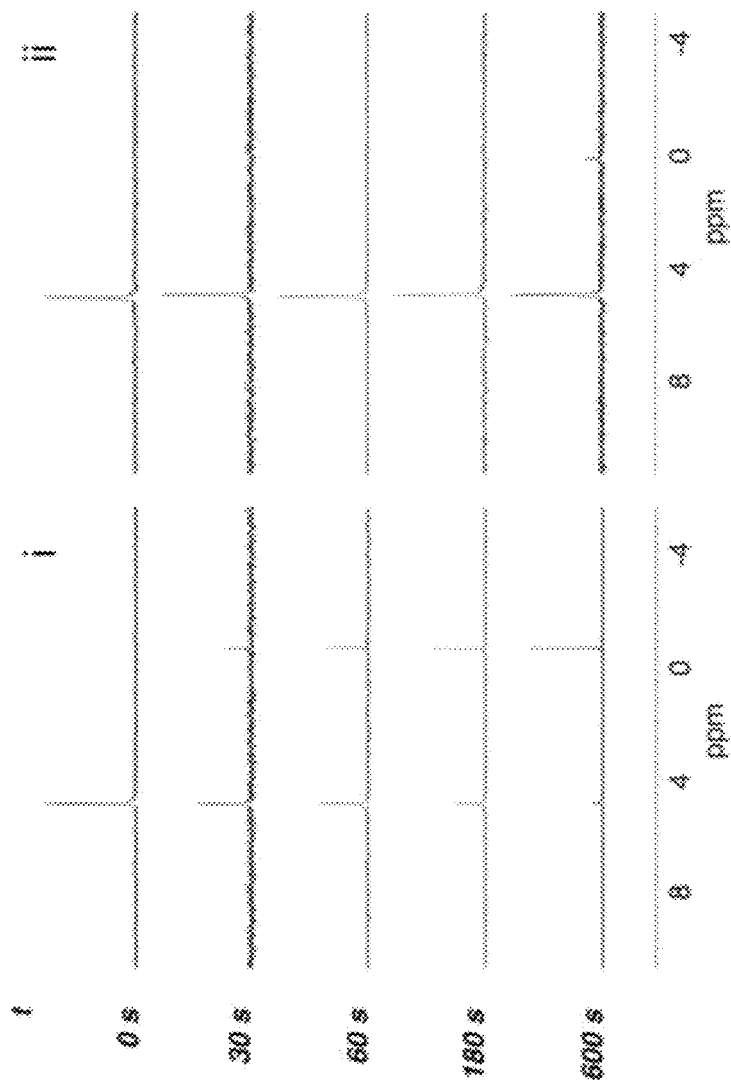
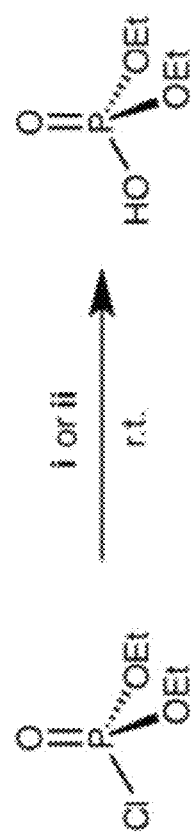
FIG. 7A
FIG. 7B

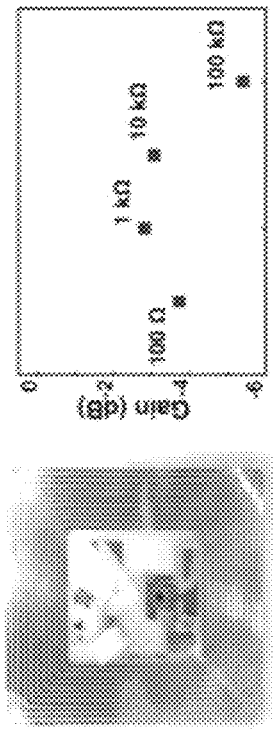
FIG. 10A
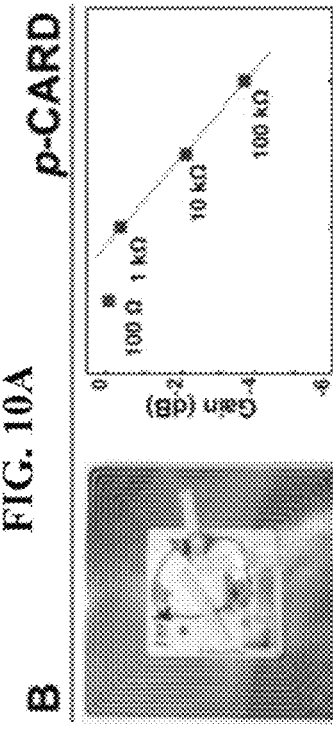
FIG. 10B
C  $Gain = -1.66 \lg R_s + 4.56$ (eq. S1)
$\Rightarrow \Delta Gain = -1.66 \lg \left( \dfrac{R}{R_0} \right)$ (eq. S2)
FIG. 10C

SYSTEM FOR DETECTING A STIMULUS INCLUDING A RADIO FREQUENCY DEVICE RESPONSIVE TO AN ANALYTE AND A PORTABLE READER

CLAIM OF PRIORITY

This application is a Continuation of U.S. application Ser. No. 16/732,095, filed Dec. 31, 2019, which is a Continuation of U.S. application Ser. No. 15/626,041, filed Jun. 16, 2017, which claims priority to U.S. Patent Application Ser. No. 62/351,881 filed on Jun. 17, 2016, each of which is incorporated herein by reference in its entirety for all purposes.

STATEMENT REGARDING FEDERALLY SPONSORED RESEARCH OR DEVELOPMENT

This invention was made with Government support under DE-AC52-07NA27344 awarded by the National Nuclear Security Administration, and W911NF-13-D-0001 awarded by the U.S. Army Research Office. The Government has certain rights in the invention.

TECHNICAL FIELD

This invention relates to wireless chemical sensors.

BACKGROUND

Development of portable and low-cost technologies for chemical and physical sensing is important for human health, safety, and quality of life. Such systems can be used for point-of-care diagnosis of disease, detection of explosives and chemical warfare agents, prevention of spoilage of food and increasing efficiency in agriculture, analysis of oil and gas, detection of petrochemical leaks and spills, monitoring of environmental pollution, detection of radiation, and monitoring of temperature or heat energy exposure. Traditional improvements in this area increase performance through modification or re-engineering of existing platforms. Such strategies may include miniaturizing components to increase portability (e.g., portable gas chromatograph or mass spectrometer) or reducing cost (e.g., increasing the efficiency of the manufacturing). While these solutions may improve existing platforms in terms of portability, they still suffer from limitations, such as being expensive, bulky, or fragile, or requiring of trained personnel to operate. Furthermore, many traditional methods of chemical sensing require physical contact of the device with the sensing element/material via wires or solid-state circuitry to acquire data.

SUMMARY

A device for detecting a stimulus can include a radio frequency identification tag including a sensor portion including an integrated circuit and a chemiresistor, where the integrated circuit and the chemiresistor are connected in parallel, where the sensor portion is configured to change resistivity when the radio frequency identification tag contacts or interacts with the stimulus, whereby the resistivity change alters an output of the radio frequency identification tag, and where the sensor portion is configured to activate the circuit or deactivate the circuit when contacted or having interacted with the stimulus.

In certain embodiments, the chemiresistor can include a plurality of nanotubes.

In certain embodiments, the chemiresistor can further include an ionic liquid.

In certain embodiments, the chemiresistor can include a plurality of conducting polymers.

In certain embodiments, the device can be a badge wearable by a person.

In certain embodiments, the badge can be for a single-use.

In certain embodiments, the nanotubes can be single walled carbon nanotubes.

In certain embodiments, the ionic liquid can be 1-butyl-3-methylimidazolium chloride.

In certain embodiments, the stimulus can include an analyte.

In certain embodiments, the analyte can be diethyl chlorophosphate.

In certain embodiments, the sensor portion can further comprise a resistor in series with the integrated circuit.

In certain embodiments, the resistor can set a threshold at which the integrated circuit is activated.

A system for detecting a stimulus can include the device described above and a reader detecting the output from the radio frequency identification tag.

In certain embodiments, the reader can be a handheld reader.

In certain embodiments, the handheld reader can be a smartphone.

In certain embodiments, the system can include a dosimeter.

In certain embodiments, the system can include a plurality of tags.

In certain embodiments, each of the plurality of tags can be capable of detecting at least one stimulus.

In certain embodiments, a food packaging including the device described above.

In certain embodiments, a breath analysis detector can include the device described above.

A method of detecting a stimulus can include detecting an output from a radio frequency identification tag including a sensor portion including an integrated circuit and a chemiresistor, where the integrated circuit and the chemiresistor are connected in parallel, where the sensor portion is configured to change resistivity when the radio frequency identification tag contacts or interacts with the stimulus, whereby the resistivity change alters an output of the radio frequency identification tag, and where the sensor portion is configured to activate the circuit or deactivate the circuit when contacted or having interacted with the stimulus.

In certain embodiments, the method can further include detecting the output of the radio frequency identification by a reader.

In certain embodiments, the reader can be a hand-held reader.

In certain embodiments, the reader can include a smartphone.

In certain embodiments, the chemiresistor can include a plurality of nanotubes.

In certain embodiments, the chemiresistor can further include an ionic liquid.

In certain embodiments, the nanotubes can be single walled carbon nanotubes.

In certain embodiments, the ionic liquid can be a solid.

In certain embodiments, the ionic liquid can be 1-butyl-3-methylimidazolium chloride.

In certain embodiments, the stimulus can include an analyte.

In certain embodiments, the analyte can be diethyl chlorophosphate.

In certain embodiments, the method can further include producing a readable signal in a reader as a result of the resistivity change.

In certain embodiments, the method can further include turning off a readable signal in a reader as a result of the resistivity change.

In certain embodiments, the output can be detectable by a reader after the output is shifted by detection of the stimulus.

In certain embodiments, the output can be detectable by a reader after the output going through a physical object.

In certain embodiments, the stimulus can contact or interact with a portion of the surface of the radio frequency identification tag.

In certain embodiments, the radio frequency identification tag does not require a power source.

In certain embodiments, the method can further include altering an electrical connection within the radio frequency identification tag.

Other aspects, embodiments, and features will be apparent from the following description, the drawings, and the claims.

BRIEF DESCRIPTION OF THE DRAWINGS

FIG. 4A shows saturation plots. FIG. 4B shows relative resistance change per minute.

FIGS. 7A-7B show $^{31}P$ NMR kinetics study of DCP hydrolysis.

FIG. 10A shows s-CARD architecture NFC tags built with a series of fixed resistors (left). and the gain vs. log(Rs) plot of s-CARD architectures (right). FIG. 10B shows p-CARD architecture NFC tags built with a series of fixed resistors (left) and gain vs. log(Rs) plot of p-CARD architectures (right). FIG. 10C shows empirically derived p-CARD architecture formula relating gain and $R_s$ (eq. S1) and empirically derived formula relating relative change in gain and the ratio of final resistance R over initial resistance $R_0$ (eq. S2).

DETAILED DESCRIPTION

Human exposure to hazardous chemicals can have adverse short- and long-term health effects. Disclosed herein is a single-use wearable hazard badge that dosimetrically detects diethylchlorophosphate (DCP), a model organophosphorous cholinesterase inhibitor simulant. Improved Chemically Actuated Resonant Devices (CARDs) are fabricated in a single step and unambiguously relate change in chemiresistance to a wireless readout. To provide selective and readily manufacturable sensor elements for this platform, an ionic liquid-mediated single walled carbon nanotube based chemidosimetric scheme with DCP limits of detection of 28 ppb was developed. In certain embodiments, the chemiresistor in this platform can further include conducting polymers. As a practical demonstration, an 8-hour workday time weighted average equivalent exposure of 10 ppb DCP effects an irreversible change in smartphone readout.

Figure 1B:
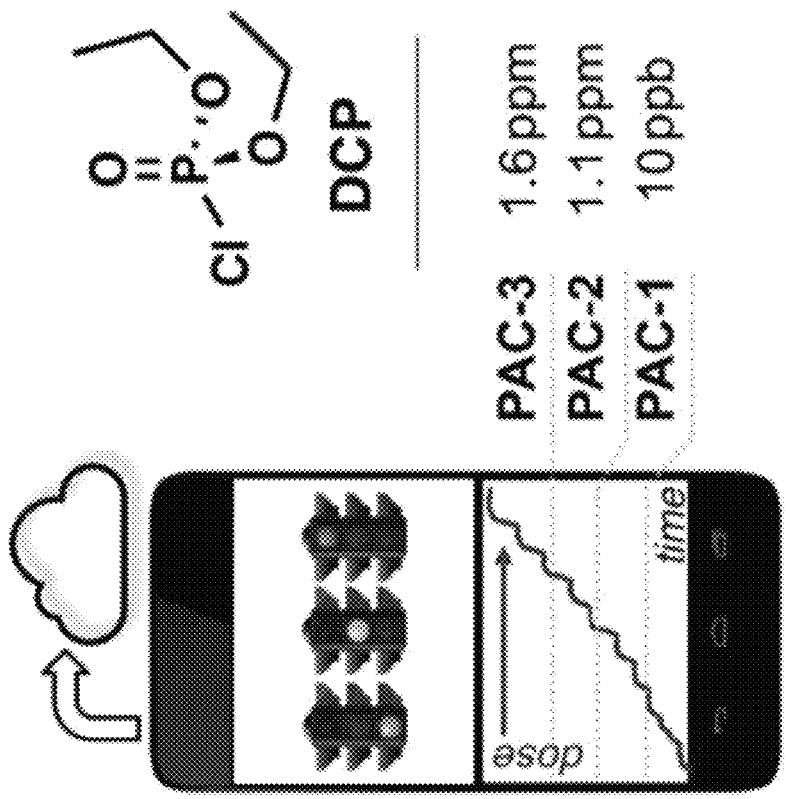
FIG. 1B shows quantification of hazardous chemical dose with a smartphone.
Figure 1A:
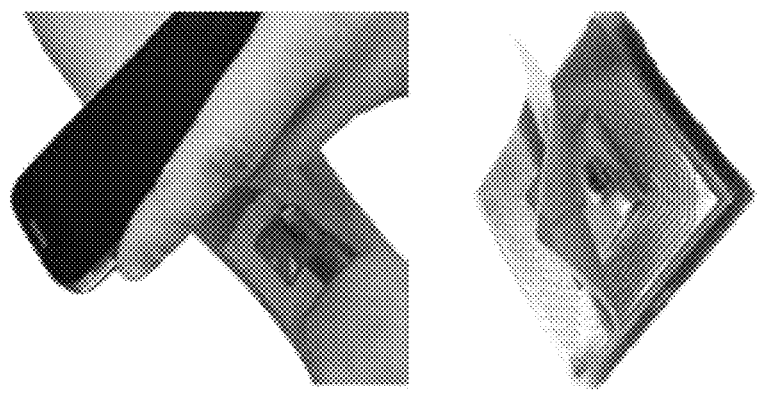
FIG. 1A shows an example of a wearable passive, disposable chemical dosimeter hazard badge.

Human exposure to hazardous chemicals in the environment, in the workplace, or in military contexts remains a critical human health concern. Furthermore, recent and continued human exposure to hazardous chemicals in 'everyday' environments has prompted heightened interest in chemical monitoring by citizens. See, D. Vallero *Fundamentals of Air Pollution*, $5^{th}$ ed., Elsevier, Waltham, 2014, pp. 139-378, S. Steinle, S. Reis, C. E. Sabel, *Sci. Total Environ.* 2013, 443, 184-193, A. Vale, T. C. Marrs, P. Rice, *Medicine* 2012, 44, 106-108, B. Erickson, *C&EN,* 2016, 94, 30-34, and R. P. Pohanish *Sittig's Handbook of Toxic and Hazardous Chemicals and Carcinogens,* 6th ed., Elsevier Science, Burlington, 2011, each of which is incorporated by reference in its entirety. Most toxic gases are not visually detectable and can be harmful at persistent exposures below the human olfaction threshold. The ability to quantify a chemical hazard dose in a temporally correlated fashion would enable real-time personalized risk assessment (FIG. 1A). A wearable passive, disposable chemical dosimeter hazard badge can be scanned periodically throughout the day. A fresh tag would be peeled off from a pack at the beginning of each time period.

Real-time, personalized situational awareness remains impractical for all but the most specialized applications: existing technological solutions are largely limited to colorimetric reagent tests such as Dräger tubes, various electronic nose technologies, and scaled down spectroscopy-based methods. See, *Dräger-Tubes & CMS-Handbook Soil, Water, and Air Investigations as Well as Technical Gas Analysis,* $16^{th}$ ed. Dräger Safety AG & Co., Lubeck, 2001, A. D. Wilson, M. Baietto, *Sensors* 2009, 9, 5099-5148, and R. Sferopoulos, *Human Protection and Performance Division,* Commonw. Aust., Victoria, 2008, DSTO-GD-0570, each of which is incorporated by reference in its entirety. These techniques' principal limitations are either cost, reliability, sensitivity, ease-of-use, physical size, power requirements, or all of the above. As a result, personal chemical dosimeters have not been broadly implemented. To address this need, a low cost, user-friendly, passive, reliable chemical hazard badge is developed to collect actionable health risk data that can be transmitted wirelessly to the cloud.

Sensing platforms that have the characteristics of being simple, inexpensive, yet sensitive and quantitative can be created. One approach to the area of chemical and physical sensing can be the development of sensing materials and devices that have the characteristics of being modular (i.e., easily modified for specific applications), wirelessly readable, and easily used and interpreted by individuals with no prior technical training.

Whitesides and co-workers have demonstrated chemical detection of analytes in biologically-relevant samples using smartphones. See, for example, Martinez, A. W. et al., Anal. Chem., 2008, 80, 3699-3707, which is incorporated by reference in its entirety. These methods involve capturing an image of a colorimetric assay using an in-phone camera and analyzing it to correlate changes in color of a dye with the presence of biologically relevant analyte. This method, however, requires line-of-sight measurement that can be affected by potential artifacts arising from lighting conditions, positional angle, or hand-movement during image acquisition.

Potyraillo et al. and others demonstrated electronic wireless detection of chemical analytes using RFID technology. See, for example, Potyrailo, R. A. et al., Anal. Chem. 2006,79, 45-51, which is incorporated by reference in its entirety. While this technology has the capability to perform non-line-of sight measurements that overcome some of the limitations of the colorimetric assays, they have limited portability as they require the use of advanced electronics devices, such as inductively coupled network analyzers or impedance spectrometers.

Studies have exploited custom-made, as well as commercially available RFID tags to monitor freshness of milk, freshness of fish, and growth of bacteria. See, for example, Tao, H. et al., Adv. Mater. 2012, 24, 1067-72; Potyrailo, R. A. et al., Battery-free Radio Frequency Identification (RFID) Sensors for Food Quality and Safety, 2012, each of which is incorporated by reference in its entirety. These studies relied primarily on correlating the changes in dielectric environment of the RFID tags (i.e., changes in C) with changes in the resonant frequency or resonant impedance of the LCR circuit. However, they are limited by a lack of selectivity toward chemical analytes and physical stimuli, and by the requirement for expensive radio frequency analysis equipment such as impedance and network analyzers for chemical detection.

Although RF technology has been recently applied towards wireless chemical sensing, current approaches have several limitations including lack of specificity to selected chemical analytes, requirements for expensive, bulky, fragile, and operationally complex impedance and network analyzers, and reliance on extensive data processing and analysis. See, Potyrailo R A, Surman C, Nagraj N, Burns A (2011) Materials and transducers toward selective wireless gas sensing. Chem Rev 111:7315-7354, Lee H et al. (2011) Carbon-nanotube loaded antenna-based ammonia gas sensor. Microw Theory Tech IEEE Trans 59:2665—2673, Potyrailo R A et al. (2009) Development of radio-frequency identification sensors based on organic electronic sensing materials for selective detection of toxic vapors. J Appl Phys 106:124902, Fiddes L K, Yan N (2013) RFID tags for wireless electrochemical detection of volatile chemicals. Sensors Actuators B Chem 186:817-823, Fiddes L K, Chang J, Yan N (2014) Electrochemical detection of biogenic amines during food spoilage using an integrated sensing RFID tag. Sensors Actuators B Chem 202:1298-1304, Occhiuzzi C, Rida A., Marrocco G, Tentzeris M M (2011) Passive ammonia sensor: RFID tag integrating carbon nanotubes. 2011 IEEE Int Symp Antennas Propag:1413-1416, each of which is incorporated by reference in its entirety.

A commercially available technology—Near Field Communication (NFC)— can be used for wireless, non-line-of-sight chemical sensing. Many modern smartphones and similar devices (tablet computers, video game controllers, and smartphone accessories) can be equipped with NFC readers operating at peak frequency of 13.56 MHz. These readers can be tuned to interact with many types of commercially available wireless "tags"—simple electrical circuits comprising an inductor (L), a capacitor (C), and an integrated circuit (resistor (R)) supported on the surface of a substrate, such as a polymeric sheet. The phone can achieve communication by powering the tag via electromagnetic induction at the specified frequency and then receiving reflected attenuated signal back from the tag. See, for example, Curty, J. P. et al., Springer, New York, 2007, pp. 49-73, which is incorporated by reference in its entirety. This technology can be used in controlling access to facilities, ticketing of events, prevention of theft, and management of inventory. This technology can be applied to chemical sensing by introducing chemiresistive materials into the circuitry of the tag. Exposure of the modified tag to chemical vapors can alter the resistance of the sensing materials, and thus the resonant frequency of the modified tag, such that it becomes readable or unreadable when probed by a smartphone reader. With this method, vapors of nitric acid, ammonium hydroxide and cyclohexanone, can be detected. This technology can be extended to physical sensors as well, such as applications in temperature, heat energy exposure or radiation sensing.

Commercially available RFID tags can be combined with a digital reader, such as a hand held frequency reader, for example a consumer electronic smartphone, resulting in a fully integrated chemical and physical sensing platform. The sensing platform can be available to anyone, including those without a technical background. This platform has advantages over existing methods of chemical and physical sensing. For example, the sensing method can be non-line-of-sight (high frequency radio waves), and can receive information from the sensor tag through solid objects such as packages, walls, wood, and other non-metallic objects. The sensing tag does not require a power source, as it receives its power from the incoming radio waves. The data-acquiring device can be any commercially available smartphone equipped with near field communication (NFC) reader capabilities, including but not limited to Samsung, LG, Google, Blackberry, etc. manufacturers. The method is simple: no technical knowledge is required to perform a measurement.

This technology can be extended to temperature, heat energy exposure and radiation sensing as well. The modification of the tag can involve integration of chemiresistive sensing materials by drawing or dropcasting onto the surface of the tag. Depending on the design, the tag can become readable or unreadable when exposed to vapors of chemicals or physical stimulus.

A stimulus can include an analyte. The stimulus can include a vapor, a gas, a liquid, a solid, a temperature change, heat energy exposure and so on. The stimulus can include an ethylene, a mold, an acid, a ketone, a thiol, an amine, and so on. Using RFID, a stimulus can be detected; for example, vapors of nitric acid and cyclohexanone can be detected; and ethylene and mold can be detected; and biological warfare agents can be detected. Cumulative exposure of analytes can be detected and quantified with a dosimeter.

A stimulus can include a physical stimulus. The physical stimulus can include light, heat, or radiation. Using RFID, a stimulus can be detected for example, exposure of a tag to heat can be detected; and radiation and light can be detected. Cumulative exposure of physical stimulus can be detected and quantified with an RFID dosimeter.

A sensing material can produce detectable change in resistance and/or capacitance upon chemical, biological, or physical changes around the sensing device. A property of a sensing material that can change upon exposure to the environment includes, but is not limited to, change in capacitance, change in resistance, change in thickness, change in viscoelasticity, or a combination thereof.

A sensing material can include a metal, an organic material, a dielectric material, a semiconductor material, a polymeric material, a biological material, a nanowire, a semiconducting nanoparticle, a carbon nanotube, a carbon nanotube network, a nanofiber, a carbon fiber, a carbon particle, carbon paste, or conducting ink, or combination thereof.

Different approaches can be taken to introduce chemical and physical sensing materials. For example, sensing materials can be introduced into two different locations within a commercial RFID tags. Sensing materials include variable resistors that alter their resistance in response to a stimulus. A stimulus can be a chemical stimulus, a physical stimulus, a biological stimulus, etc. The detection of a stimulus can be achieved by switching the tag between a "readable" and "not readable" state, by exposure to a stimulus, such as chemical vapors or changes in temperature or heat energy exposure, for example.

When a stimulus contacts or interacts with a sensor, the resistivity can change. The contact or interaction can produce a readable signal in a hand held frequency reader as a result of the resistivity change. Alternatively, the contact or interaction can turn off a readable signal in a hand held frequency reader as a result of the resistivity change. Output can be detected after the output is shifted by detection of the stimulus. Even after going through a physical object, the output can still be detected. Detecting the stimulus is not limited to the frequency output, but can include, but is not limited to, a change in frequency, a change in q factor, a change in bandwidth, and a combination of these. These changes can result in increasing or decreasing the power transferred between the reader and radio frequency identification tag. Increasing or decreasing the power transferred between the reader and radio frequency identification tag can result in a change of the readout of the tag.

In one approach, a specific electric connection within an RFID tag can be disrupted, for example by cutting, and this connection can be reestablished by deposition of a chemiresistive sensing material by either drawing or dropcasting. An RFID tag can include an integrated circuit (IC) containing magnetic memory material where the tag identification is stored. Depending on the sensing material and the stimulus, the tag can become readable and is classified as a "turn ON sensor," or become unreadable and is classified as a "turn OFF sensor".

In one method, the tag is not readable by a reader when no stimulus is present, because the resistance of the sensor is too high. When the tag is placed in the presence of a stimulus that causes the sensor to change its resistance, the tag can become readable once the resistance value crosses a threshold value. This is a turn-on sensing method.

In another method, the tag can be readable by a reader when no analyte is present, because the resistance of the sensor is high enough to allow current to flow through the integrated circuit. When the tag is placed in the presence of a stimulus that causes the sensor to change its resistance, the tag can become unreadable once the resistance value drops below a certain threshold value. This is a turn-off sensing method.

In another method, instead of a turn-on sensing or a turn-off sensing, a series of data can be collected, which can provide a quantitative analysis of a stimulus.

In another method, parallel integration can be used to integrate a sensing material into a portion of the tag containing the integrated circuit by drawing or dropcasting. This approach can "turn ON" or "turn OFF" detection of a stimulus, and can be complimentary to the first approach because requirements for resistance of the deposited sensing material can be different (which may have an effect on the dynamic range and the detection limit of chemical sensors towards different analytes).

A radio frequency identification tag does not have to require a power source. RFID tags can be either passive, active or battery-assisted passive. An active tag has an on-board battery and periodically transmits its signal. A battery-assisted passive has a small battery on board and is activated when in the presence of a RFID reader. A passive tag has no battery.

When detecting a stimulus comprising detecting an output from a radio frequency identification tag including a sensor portion, the stimulus does not have to contact or interact with the entire surface of the tag. The sensor portion has a surface area less than the surface area of the radio frequency identification tag. The sensor portion can be located on a portion of a surface of the radio frequency identification tag, and the stimulus can contact a portion of the surface of the radio frequency identification tag. In addition, the sensor portion can have multiple sensing locations, and a single tag can be used to detect more than one stimulus.

A system for detecting a stimulus comprising a radio frequency identification tag can include a sensor portion, the sensor portion configured to change resistivity when the radio frequency identification tag contacts or interacts with the stimulus, whereby the resistivity change alters an output of the radio frequency identification tag, and a detector detecting the output from the radio frequency identification tag. The detector can include a reader. The reader can include a hand held frequency reader. A method of detecting a stimulus can include detecting an output from a radio frequency identification tag including a sensor portion.

The system can include a real time sensor. The system can include a dosimeter, such as a radiation dosimeter, a chemical warfare agent dosimeter, or an analyte dosimeter, such as, for example, an ethylene dosimeter, a sulfur dosimeter, or an ozone dosimeter. The system can be used to monitor pollutants or chemicals relevant to occupational safety. Pollutants or chemicals can include fumes from automotive/equipment exhaust, volatiles from manufacturing, painting, or cleaning, or vapors in underground mines.

A sensor can include an electronic circuit comprising electronic components. Electronic components can include resistors, transistors, capacitors, inductors and diodes, connected by conductive wires or traces through which electric current can flow. The electrical connection within the radio frequency identification tag can be altered. The resistivity of the sensor can change when the sensor is exposed to a stimulus. Contacting or interacting with a stimulus can close the circuit or open the circuit, or otherwise alter the properties of the circuit.

A sensor can include a sensing material such as a metal, an organic material, a dielectric material, a semiconductor material, a polymeric material, a biological material, a nanowire, a semiconducting nanoparticle, a carbon nanotube, a nanofiber, a carbon fiber, a carbon particle, carbon paste, or conducting ink, or combination thereof. A sensing material can include organic electronics materials, doped conjugated polymers, or inorganic materials. A sensing material can include biological molecule receptors, living cells, antibodies, aptamers, nucleic acids, functionalized biological molecules, and so on.

A tag for detecting a stimulus comprising a radio frequency identification tag can include a sensor portion, the sensor portion configured to change resistivity when the radio frequency identification tag contacts or interacts with the stimulus, whereby the resistivity change alters an output of the radio frequency identification tag, wherein the sensor portion includes a circuit, and wherein the sensor portion is configured to close the circuit or open the circuit when contacted or having interacted with the stimulus. The tag can be worn as a badge for occupational health and safety personnel, military personnel, etc., detecting a hazardous analyte or radiation.

A tag can include a substrate material. The substrate can include paper, plastic, a polymer, a metal, a metal oxide, a dielectric material, wood, leaves, skin, tissue, and so on. The substrate can include a metal oxide material. The substrate can be flexible; the substrate can be flat. The tag can also be embedded inside other objects (e.g., inside a capsule or a wall) or inside living systems (e.g., implanted inside a body).

A tag can include an antenna, providing a link between a frequency reader and a tag, receiving and transmitting a signal, and serving as a conduit that moves data back and forth. The antenna can include coils surrounding a sensor; the antenna can include a dipole antenna. A tag can include an antenna group including a plurality of antennas or an antenna array.

The ability to easily detect the existence of an analyte on a base signal using an ON/OFF binary detection method is of increasing interest in today's society. A system using a portable reader, such as a smartphone, enables everyone to determine the status of certain analytes anywhere without complicated analysis of a signal. When the amount of an analyte changes, a handheld frequency reader can turn on or turn off a signal, sending a notification of the presence or absence of the analyte. Another advantage of using a smartphone is that it carries within it many additional capabilities that can be coupled with chemical sensing to increase utility. For instance, a smartphone reader can identify a chemical spill and immediately send an emergency text or email alert identifying position of a spill using GPS. Another example could be wireless networks that monitor spatiotemporal changes in concentrations of chemical emissions and send emergency alerts when safe thresholds are exceeded. Coupling of such capabilities can enable unprecedented utility of chemical sensors in everyday life.

A tag can serve as a binary logic element providing either a "1" or a "0" as pre-defined by functional sensor material, which offers advantages in terms of simplicity of implementation and does not require any sophistication by the end user. If viewed as a binary logic element, the tag could be used in further elaborations of that logic. For instance, a unique combination of the readout of multiple tags could be assigned to a specific meaning. For example, if three separate tags are "coded" for three separate analytes by virtue of the sensor materials used to make them, then $2^3$ possible combinations exist, which could each mean something unique and significant. For example, if those analytes were food related, then one could possibly determine which type of food the sensors are attached based on a combination of tag read-out, within a certain probability. Another example would be three tags that are "coded" with the same sensor material that has been designed to react at different concentrations of analyte. The combination of tag readout would allow one to determine, within some margin of error, the concentration of the analyte of interest.

The binary on/off readability of CARDs by the smartphone can be a powerful approach for converting analog physical inputs (presence or absence of a chemical vapor within a defined threshold) into a digitized output (1 and 0, respectively) that conveys meaningful information about the local chemical environment of the CARDs. The advantage of a binary-readout is that it is the simplest possible output representation of input information, and hence allows modular multiplexing of different CARD combinations. Taken together, discrimination and identification of multiple analytes can be achieved with a smartphone by converting the output of binary CARDs ("on"/"off") into multi-CARD logic (sequences of 0s and 1s). This analytical approach has practical limitations in its implementation; however, it may be particularly useful in resource-constrained scenarios or high throughput applications where information about the presence or absence of specific chemicals at specified thresholds is critically important. Such applications may include detection of an acceptable threshold (e.g., permissible exposure limit for a chemical) that provides valuable actionable information in dynamic, complex environments (e.g., chemical release within a public space). Even under circumstances wherein the chemical of interest can be readily detected by the human nose, a differentiating feature of a smartphone-based sensing strategy over human-olfactory detection or visual inspection of a colorimetric test is the ability to efficiently bring sensed information into the information technology infrastructure.

An inexpensive, simple, rapid, and modular approach for converting commercially available NFC tags into chemically actuated devices can communicate with a smartphone via radio waves. This approach enables electronic wireless, non-line-of-sight detection and discrimination of gases and vapors at part-per-million and part-per-thousand concentrations. This technology provides binary ("on"/"off") information about the presence or absence of a chemical analyte regarding designated concentration thresholds, (e.g., NIOSH STEL) within the local environment of the sensor tag, and is capable of differentiating multiple concentrations of one analyte or multiple analytes using multi-tag logic. The general sensing strategy involving wireless communication between NFC tags and smartphones is modular and can be generalized to incorporate many types of chemiresponsive materials to enable selective detection of diverse chemical changes. Nevertheless, the significant challenges that remain to realize the full potential of this wireless sensing approach includes: (i) chemical and materials science innovations to improve the sensitivity and selectivity of chemiresponsive materials to chemical analytes; (ii) improving device-to-device performance reproducibility by advancing the state-of-the-art of nanostructured carbon deposition techniques and; (iii) enabling continuum measurement CARD readout capabilities. The combination of chemical sensing with other capabilities within the smartphone (e.g., GPS) may enable additional utility in applications involving tracking and tracing. As a result of the portability and increasingly ubiquitous use of smartphones and mobile devices, this platform can enable applications in personalized and widely distributed chemical sensing wherein the acquisition of chemical or physical information was previously unattainable.

A method and a system of converting inexpensive commercial NFC tags into chemical sensors that detect and discriminate analytes at part-per-thousand and part-per-million concentrations have been previously disclosed. See, U.S. Patent Application Ser. No. 14/528,856, which is incorporated by reference in its entirety. This effort merges rational design of conductive nanostructured materials for selective chemical sensing with portable and widely distributed NFC technology to deliver a new method of acquiring chemical information about an NFC tag's local environment.

Two-step conversion of NFC tags into Chemically Actuated Resonant Devices (CARDs) can enable semi-quantitative, selective detection of chemical gases with a smartphone. See, U.S. Patent Application Ser. No. 14/528,856 and J. M. Azzarelli, K. A. Mirica, J. B. Ravnsbæk, T. M. Swager, *Proc. Natl. Acad. Sci.* 2014, 111, 18162-18166, each of which is incorporated by reference in its entirety. However, ultra-trace (sub part-per-million) sensing and dosimetric detection remain challenging with the initial designs. See, S. Goswami, S. Das, K. Aich, *RSC Adv.* 2015, 5, 28996-29001, and A. M. Costero, M. Parra, S. Gil, R. Gotor, R. Martínez-Máñez, F. Sancenón, S. Royo, *European J. Org. Chem.* 2012, 4937-4946, each of which is incorporated by reference in its entirety. To address these challenges, key improvements are disclosed here to both the circuit design as well as new single walled carbon nanotube (SWCNT)-based chemiresistive dosimetric materials.

Figure 2A:
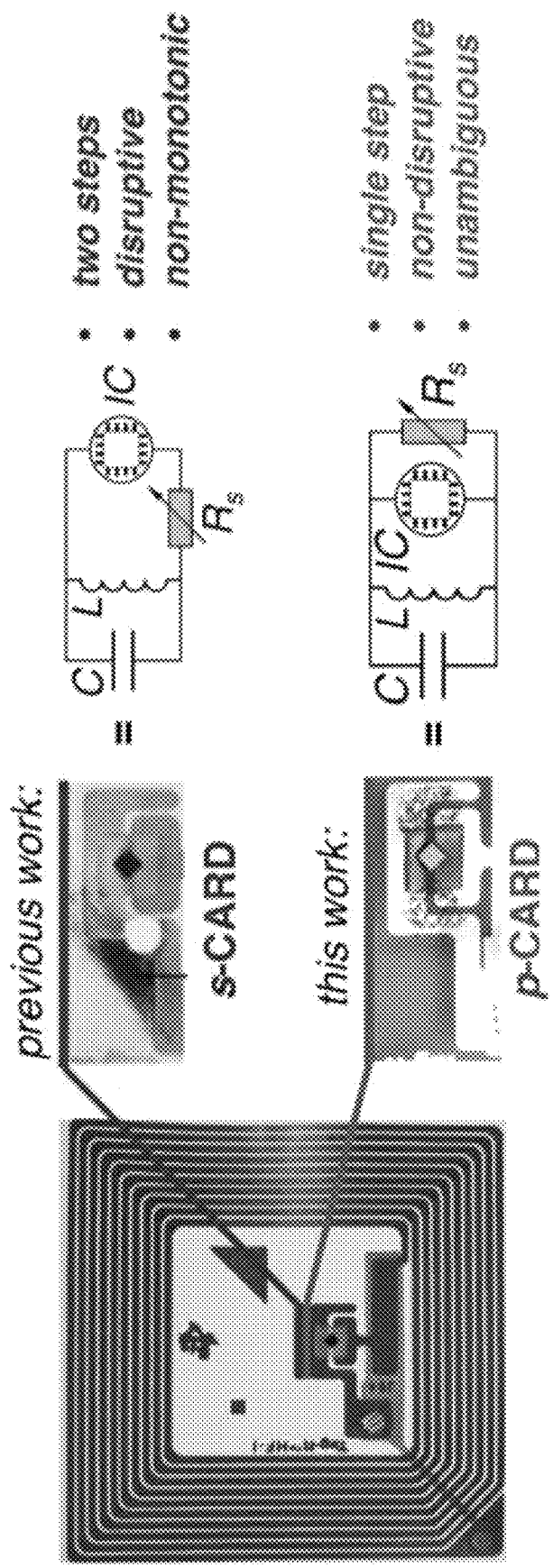
FIG. 2A shows single-step non-disruptive conversion of a commercial NFC tag to a p-CARD and comparison to the first generation design.

In this first generation CARD platform (series-CARD, or s-CARD), the chemiresistor ($R_s$) is incorporated in series with the NFC integrated circuit (IC) in a two-step method. This method involves the disruption and recompletion of the circuit (FIG. 2A). To create an s-CARD, a hole is punched removing some of the aluminum lead material and disrupting the circuit, which is reconnected by the chemiresistor. To create a p-CARD, the material is deposited on the aluminum leads connecting the IC. Note that the p-CARD photograph has opposite contrast (aluminum metal is bright) to reveal the deposited chemiresistor. The raw chemical information that the chemiresistor collects is converted and wirelessly transmitted, mainly in the form of device resonant frequency ($f_0$) amplitude, gain (in dB).

Although the s-CARD proved successful in selectively detecting chemically-diverse analytes at parts-per-million (ppm) levels, its circuit structure can introduce physical constraints to the response magnitude corresponding to a certain change in the sensor resistance ($\Delta Gain/\Delta R_s$). The gain readout of a series of s-CARDs with fixed resistors ($R_s$) was systemically examined in place of chemiresistors. These resistors ranged from 100Ω to 100Ω, which encompassed the typical dynamic range of the CNT-based chemiresistors (1 kΩ to 100 kΩ. As shown in FIG. 2B-i, the device resonated in all cases, and a non-monotonic change in the gain readout was observed as $R_s$ increased (FIG. 2B-i, inset). This resulted in a minimal gain difference observed between $R_s$=1 kΩ and 10 kΩ. More importantly, the non-monotonicity leads to ambiguous results when the device is operating within a large dynamic gain range. Disclosed herein is a wearable, battery free, single-use chemical hazard badge that costs less than $1, is combustible or recyclable and therefore environmentally friendly, and is smartphone-communicable (FIG. 1B). Quantification of hazardous chemical 'dose' with a smartphone enables facile information collection to a centralized database, via 'the cloud.' Standardized decisions can be informed by pre-defined protective action criteria levels associated with equivalent exposure time weighted average hazardous chemical concentration. Passive radio frequency communication devices, such as Near Field Communication (NFC) tags, meet these requirements. See, V. Coskun, B. Ozdenizci, K. Ok, *Wirel. Pers. Commun.* 2013, 71, 2259-2294, which is incorporated by reference in its entirety.

Figure 2B:
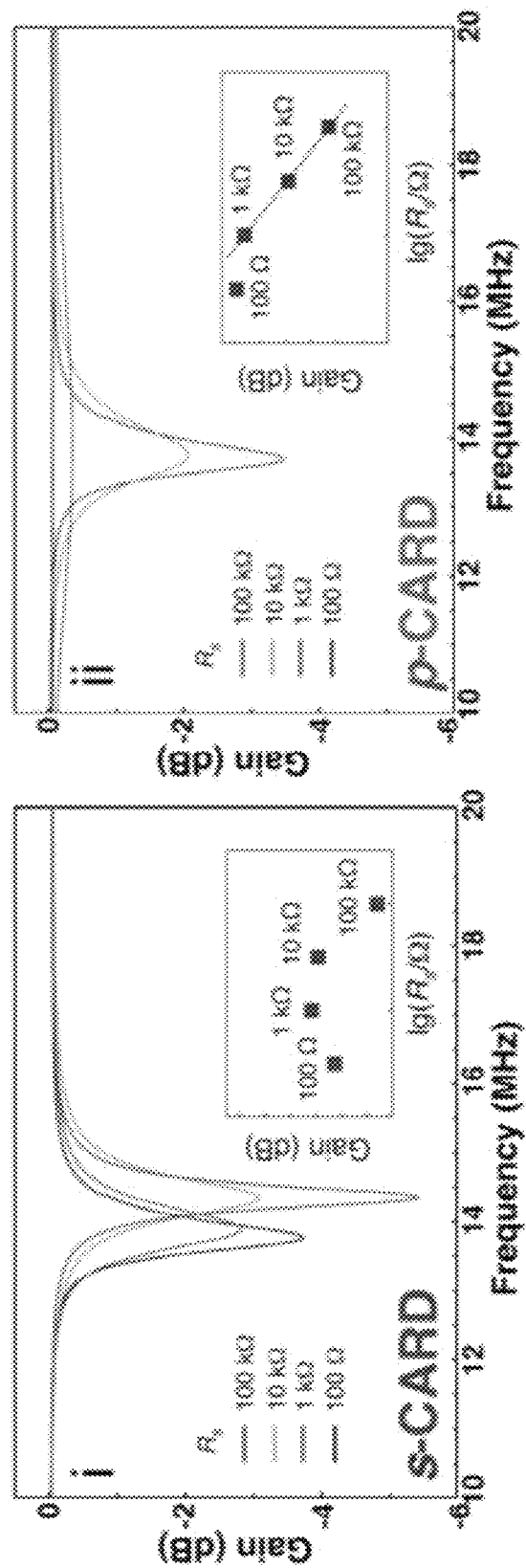
FIG. 2B shows resonance-frequency traces for s-CARD (i) and p-CARD (ii) with varying Rs. Respective gain values measured for each Rs (inset).

It was hypothesized that incorporation of the chemiresistor in parallel with the integrated circuit would serve to overcome these drawbacks associated with s-CARDs. Such a modification process produced a new type of CARD platform: parallel-CARD, or p-CARD. For a proof of concept, parallel fixed resistors ranging from 100Ω to 100Ω were used to construct a series of p-CARDs. Their gain readouts were measured. As shown in FIG. 2B-ii, as $R_s$ increased, the device underwent a monotonic decrease in gain and proceeded from non-resonant to resonant. The gain-log $R_s$ relationship was linear from 1 kΩ through 100 kΩ (FIG. 2B-ii, inset).

The importance of practicability in the fabrication procedure of a new device structure should not be understated. In this regard, the p-CARD design is advantageous; it does not require disruption of the existing RFID circuit and is a single step to fabricate. The p-CARD is created by simple deposition of chemiresistive material between the leads connecting the IC (FIG. 2A). This non-disruptive modification method not only results in more consistent device performance but also makes p-CARDs amenable to inkjet printing and roll-to-roll manufacturing processes. See, L. Yang, R. Zhang, D. Staiculescu, C. P. Wong, M. M. Tentzeris, *Antenna Wirel. Propag. Lett. IEEE* 2009, 8, 653-656, K. Kordas, T. Mustonen, G. Toth, H. Jantunen, M. Lajunen, C. Soldano, S. Talapatra, S. Kar, R. Vajtai, P. M. Ajayan, *Small* 2006, 2, 1021-1025, R. A. Potyrailo, A. Burns, C. Surman, D. J. Lee, E. McGinniss, *Analyst* 2012, 137, 2777, W. Lee, H. Koo, J. Sun, J. Noh, K.-S. Kwon, C. Yeom, Y. Choi, K. Chen, A. Javey, G. Cho, *Sci. Rep.* 2015, 5, 17707, and M. Jung, J. Kim, J. Noh, N. Lim, C. Lim, G. Lee, J. Kim, H. Kang, K. Jung, A. D. Leonard, et al., *IEEE Trans. Electron Devices* 2010, 57, 571-580, each of which is incorporated by reference in its entirety. With p-CARD platform in hand, a DCP-responsive dosimetric SWCNT chemiresistor was developed based on the irreversible hydrolysis of DCP. See, J. F. Fennell, S. F. Liu, J. M. Azzarelli, J. G. Weis, S. Rochat, K. A. Mirica, J. B. Ravnsbwk, T. M. Swager, *Angew. Chemie Int. Ed.* 2015, 55, 1266-1281, K. Kim, O. G.Tsay, D. A. Atwood, D. G. Churchill, *Chem. Rev.* 2011, 111, 5345-5403, S.-Y. Moon, Y. Liu, J. T. Hupp, O. K. Farha, *Angew. Chem. Int. Ed.* 2015, 54, 6795-6799; *Angew. Chem.* 2015, 127, 6899-6903, E. López-Maya, C. Montoro, L. M. Rodriguez-Albelo, S. D. A. Cervantes, A. A. Lozano-Pérez, J. L. Cenis, E. Barea, J. A. R. Navarro, *Angew. Chem. Int. Ed.* 2015, 54, 6790-6794; *Angew. Chem.* 2015, 127, 6894-6898, and H. Sohn, S. Létant, M. J. Sailor, W. C. Trogler, *J. Am. Chem. Soc.* 2000, 122, 5399-5400, each of which is incorporated by reference in its entirety. To enhance the response by accelerating hydrolysis, SWCNTs were targeted in ionic liquids. See, T. Welton, *Chem. Rev.* 1999, 99, 2071-2083, P. Pavez, D. Millán, C. Cocq, J. G. Santos, F. Nome, *New J. Chem.* 2015, 39, 1953-1959, P. Pavez, D. Millán, C. J. I. Morales, E. A. Castro, C. López A., and J. G. Santos, *J. Org. Chem.* 2013, 78, 9670-9676, each of which is incorporated by reference in its entirety. In addition to creating solution-phase reactivity at the SWCNT surface, ionic liquids (IL) have been shown to partially debundle SWCNTs when the two components are ground together in the solid state or when a mixture of SWCNTs and IL are sonicated together in the presence of co-solvents. See, T. Fukushima, A. Kosaka, Y. Ishimura, T. Yamamoto, T. Takigawa, N. Ishii, T. Aida, *Science* 2003, 300, 2072-2074, T. Fukushima, T. Aida, *Chem. Eur J.* 2007, 13, 5048-5058; c) S. Zhang, Q, Zhang, Y. Zhang, Z. Chen, M. Watanabe, Y. Deng, *Prog. Mater. Sci.* 2016, 77, 80-124, and M. Tunckol, J. Durand, P. Serp, *Carbon* 2012, 50, 4303-4334, each of which is incorporated by reference in its entirety. Despite these advantages, SWCNT/ILs are not an established chemiresistor platform. For a graphene-IL based quartz crystal microbalance gas sensor, see Q. Ji, I. Honma, S.-M. Paek, M. Akada, J. P. Hill, A. Vinu, K. Ariga, *Angew. Chem.* 2010, 122, 9931-9933; *Angew. Chem. Int. Ed.* 2010, 49, 9737-9739; SWCNT-IL hybrid has been used as electrode material for voltammetric sensing, and S. Fan, F. Xiao, L. Liu, F. Zhao, B. Zeng, *Sens. Actuators B-Chem.* 2008, 132, 34-39, each of which is incorporated by reference in its entirety.

Diethyl chlorophosphate (DCP) was targeted in the development of a prototype chemical hazard dosimeter. DCP has been studied as a target analyte for chemical sensors mainly as a chemical warfare nerve agent (NA) simulant. See, X. Zhou, Y. Zeng, C. Liyan, X. Wu, J. Yoon, *Angew. Chem. Int. Ed.* 2016, 55, 4729-4733, C. Belger, J. G. Weis, E. Egap, T. M. Swager, Macromolecules, 2015, 48, 7990-7994, Z. Lei, Y. Yang, *J. Am. Chem. Soc.* 2014, 136, 6594-6597, H. J. Kim, J. H. Lee, H. Lee, J. H. Lee, J. H. Lee, J. H. Jung, J. S. Kim, *Adv. Funct. Mater* 2011, 21, 4035-4040, and S.-W. Zhang, T. M. Swager, *J. Am. Chem. Soc.* 2003, 125, 3420-3421, each of which is incorporated by reference in its entirety. It is also a chemical analog of cholinesterase inhibiting organophosphate pesticides. See, *Toxicology of Organophosphate & Carbamate Compounds*, (Ed.: R. C. Gupta), Elsevier Academic Press, Burlington, 2006, pp. 103-160; 209-217; 599-655, which is incorporated by reference in its entirety. For chemical hazards like DCP, time-weighted-average (TWA) permissible exposure limits are the most relevant parameter in dictating the necessity and type of protective actions to be taken. Ideal chemical hazard dosimeters allow instantaneously assess of a TWA exposure based on temporally-correlated chemical dose information. For instance, the US Department of Energy has established 'protective action criteria' levels (PAC) for over 3,000 hazardous substances, including DCP. See, *Temporary Emergency Exposure Limits for Chemicals: Methods and Practice*, U.S. Dept. Energ., Washington, D.C., 2008, DOE-HDBK-1046-2008, and *Protective Action Criteria Rev.* 28A Table 2, U.S. Dept. Energ. Subcommittee on Consequence Assessment and Protective Actions (SCAPA), each of which is incorporatd by reference in its entirety. Accordingly, hazard badges can be designed to display scenario-informed options on a smartphone at dosage levels that induce mild, transient health effects (PAC-1), serious health effects that could inhibit ability to further protect oneself (PAC-2), or life threatening health effects (PAC-3). Furthermore, personal exposure information can be synchronized with a cloud database to expose spatio-temporal trends (see N. Cressie, C. K. Wilke in *Statistics for Spatio-Temporal Data*, John Wiley & Sons, Hoboken, 2011, pp. 243-356, which is incorporated by reference in its entirety) and enable emergency decision-making by a second party in the case of the hazard badge-wearer incapacitation.

In other applications, the device disclosed herein can be used to detect any chemicals in liquid or gaseous fluids. Chemical sensors are of interest for applications in homeland security, public safety, occupational health and safety, industrial fluid analysis, food and beverage analysis, and in human healthcare and therapeutic applications. In certain embodiments, the sensor can be incorporated into food packaging. In certain embodiments, the sensor can be incorporated in a breath analysis detector to analyze and determine what a person has been exposed to or if they have a disease. A breath analysis detector can detect volatile compounds in breath, such as alcohol, ketones and other volatile compounds that can indicate physiological condition of an individual.

The response of p-CARDs fabricated with SWCNT/IL composites to DCP was tested in nitrogen ($N_2$). A combination of SWCNT and 1-butyl-3-methylimidazolium chloride (BMIMCl) showed a good, irreversible response. Previous work has shown that small molecule selectors incorporated into chemiresistor formulations can selectively enhance the resistive response to gas analytes. See, K. A. Mirica, J. M. Azzarelli, J. G. Weis, J. M. Schnorr, T. M. Swager, *Proc. Natl. Acad. Sci.* 2013, 110, E3265—E3270, which is incorporated by reference in its entirety. By incorporating 2-(2-hydroxy-1,1,1,3,3,3-hexa-fluoropropyl)-1-naphthol (HFIPN) as a hydrogen-bonding chelator/catalyst (see, F. Wang, T. M. Swager, *J. Am. Chem. Soc.* 2011, 133, 11181-11193, and J.—P. Bégué, D. Bonnet-Delpon, B. Crousse, *Synlett* 2004, 18-29, each of which is incorporated by reference in its entirety) into the mixture, a 3.3× improvement in response to DCP was realized (FIG. 3A). When exposed to DCP (1 ppm) for 50 seconds, p-CARDs fabricated with HFIPN (blue bar, left) had a 3.3× larger magnitude of response than those fabricated without HFIPN (red bar, right).

The irreversible response and significant enhancement associated with the BMIMCl/l HFIPN-based chemiresistor was consistent with observed hydrolysis kinetics of DCP in solution (FIGS. 7A-7B). At r.t., DCP undergoes only minor hydrolysis after stirring in $CD_3CN$ for 10 min, even in the presence of excess water (8 equiv.) as monitored by $^{31}P$ NMR (Scheme 1, conditions ii: DCP: δ~4.8 ppm). In contrast, when DCP was added to a mixture of HFIPN and BMIMCl (a minimal amount of $CD_3CN$ was added to obtain a liquid mixture) in the absence of any additional water, instantaneous hydrolysis occurred with the trace water present under ambient atmosphere (conditions i). Specifically, a significant portion was hydrolyzed within a few seconds, indicated by the emerging signal of diethylphosphoric acid at δ~−0.5 ppm. Nearly full conversion was observed within 10 min.

Figure 3B:
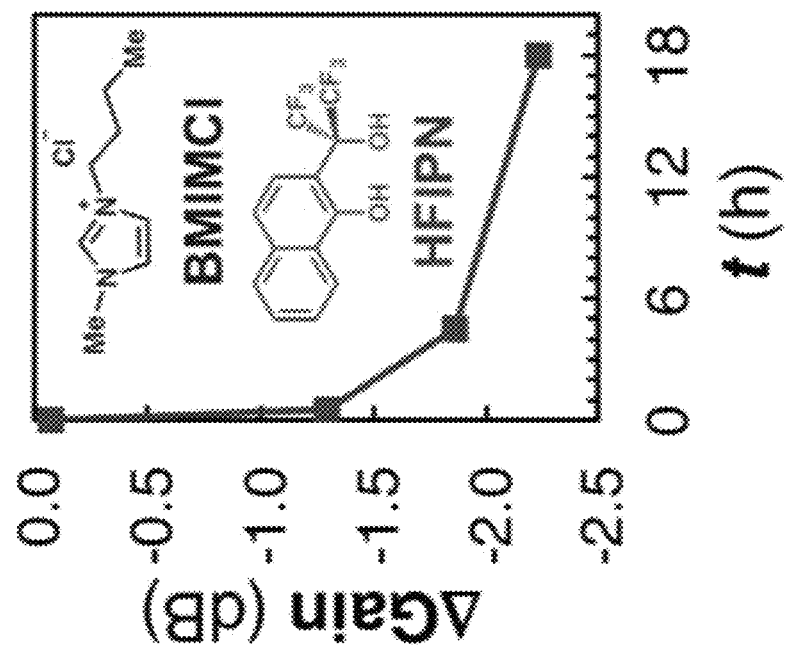
FIG. 3B shows the magnitude of response as a function of device age.
Figure 3A:
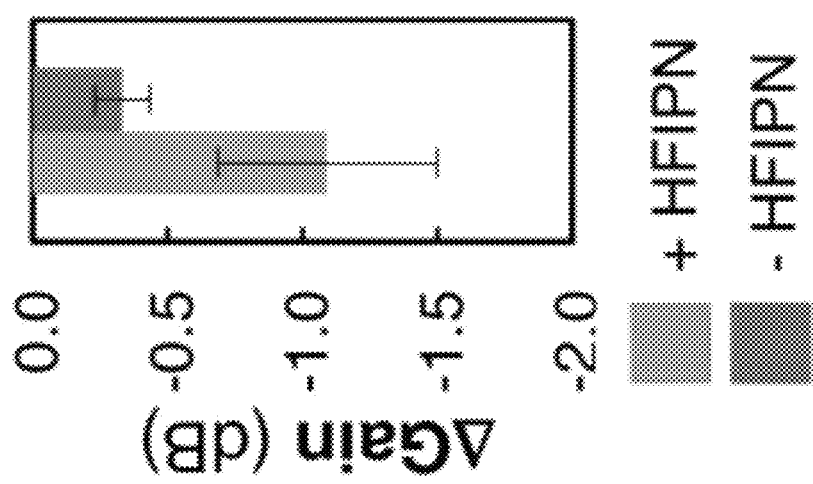
FIG. 3A shows the responses of p-CARDs fabricated with or without HFIPN.
Figure 3C:
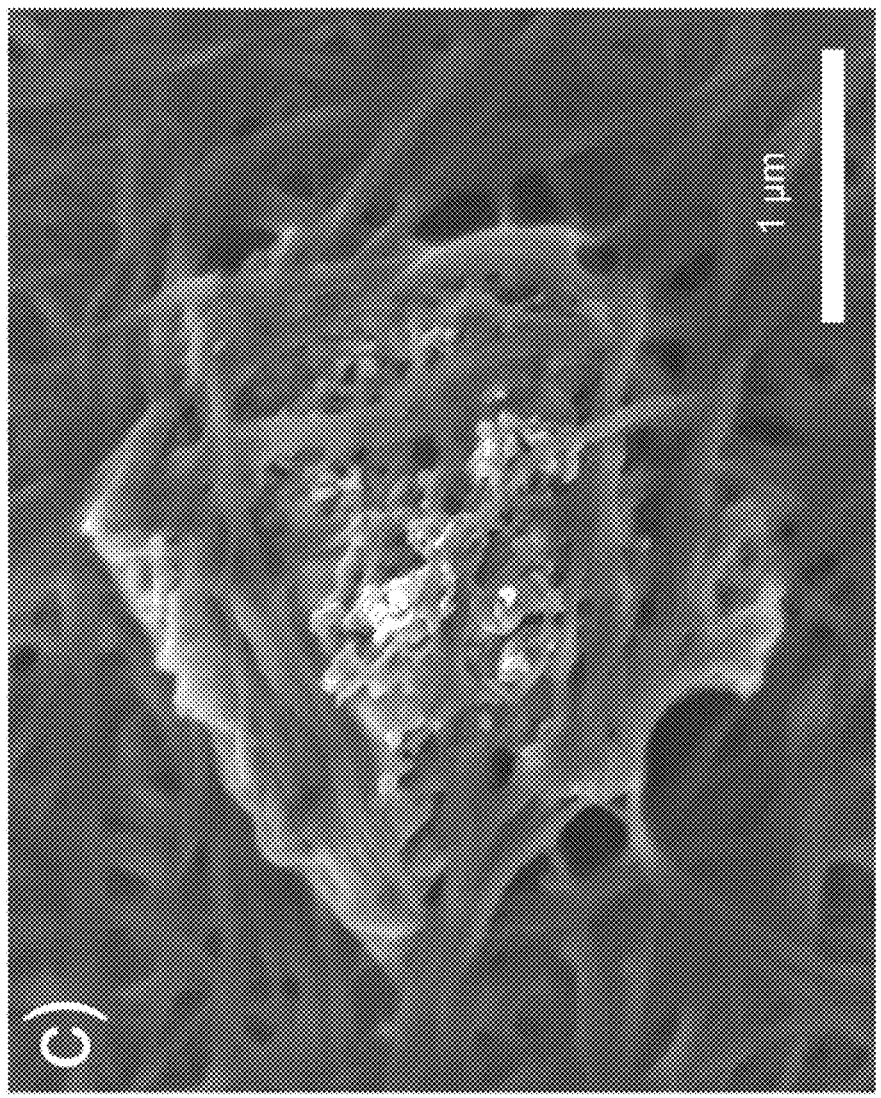
FIG. 3C shows SEM image of a typical SWCNT-wrapped microcrystal.
Figure 14:
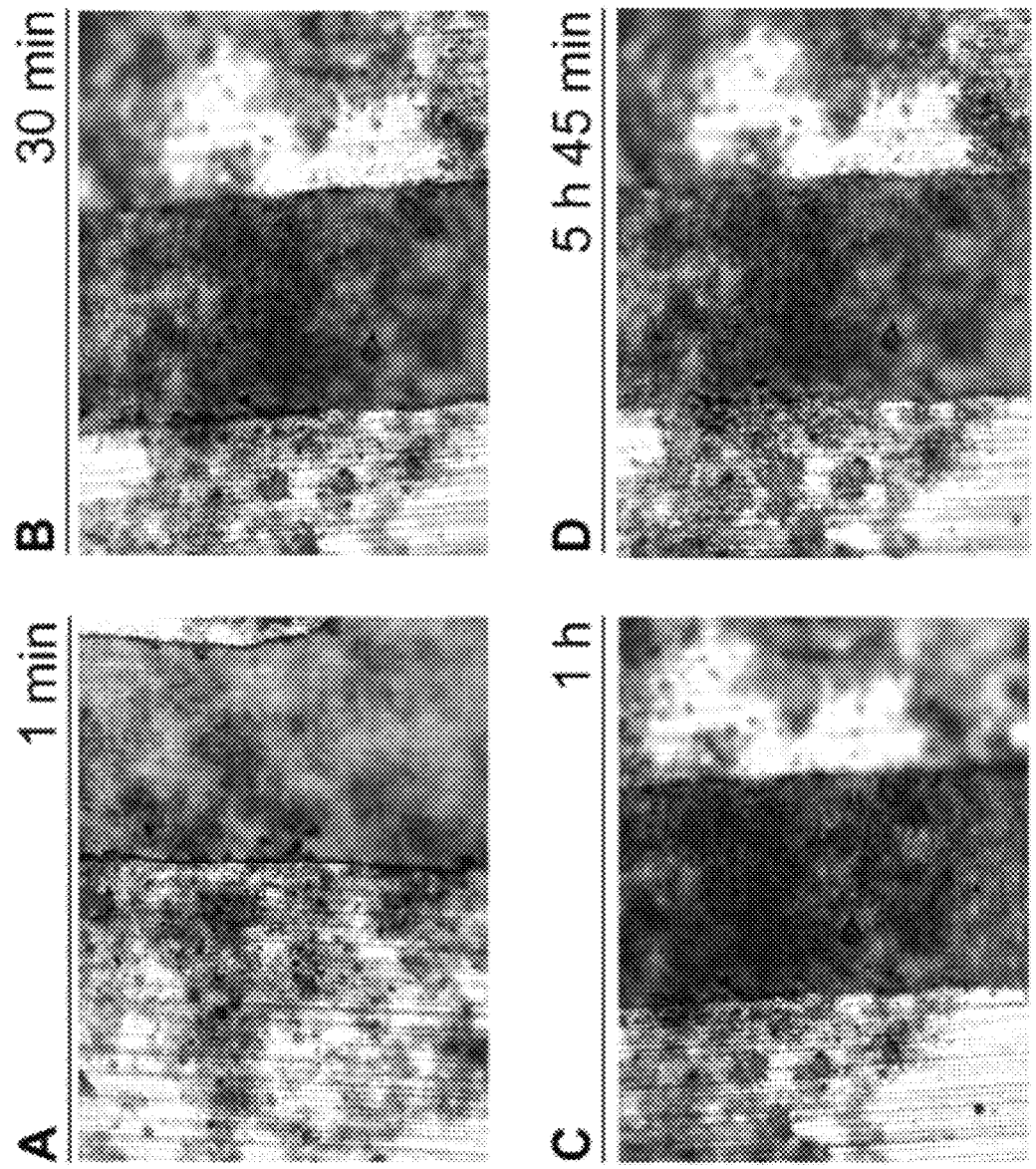
FIG. 14 shows optical microscopy images (10× objective) of p-CARD chemiresistor changing over time.

Upon a more thorough investigation, there was a maturing process with the SWCNT/BMIMCl system, accompanied by two coinciding observations: 1) p-CARD baseline (gain) drift was effectively zero and 2) the magnitude of the response to DCP increased substantially as a function of time, reaching a maximum after ~18 h (FIG. 3B). Magnitude of response (ΔGain) as a function of device 'age.' Blue squares represent different devices. Visual inspection and optical microscopy confirm time-dependent crystallization of BMIMCl at the surface of p-CARD (FIG. 14). Scanning electron microscopy (SEM) revealed the formation of SWCNT-wrapped microcrystal structures (FIG. 3C). It was hypothesized that such structures could increase SWCNT surface area and thus lead to an enhanced response. This is consistent with the observation that p-CARDs fabricated with 1-butyl-3-methylimidazolium type ILs that are liquids at room temperature (anion=hexafluorophosphate, bromide, or iodide) did not demonstrate this behavior. Recent reports suggest solid-phase ILs hold promise as a tunable class of materials for a broad array of applications. See, I. M. Warner, B. El-zahab, N. Siraj, *Anal. Chem.* 2014, 86, 7184-7191, which is incorporated by reference in its entirety.

Figure 4A:
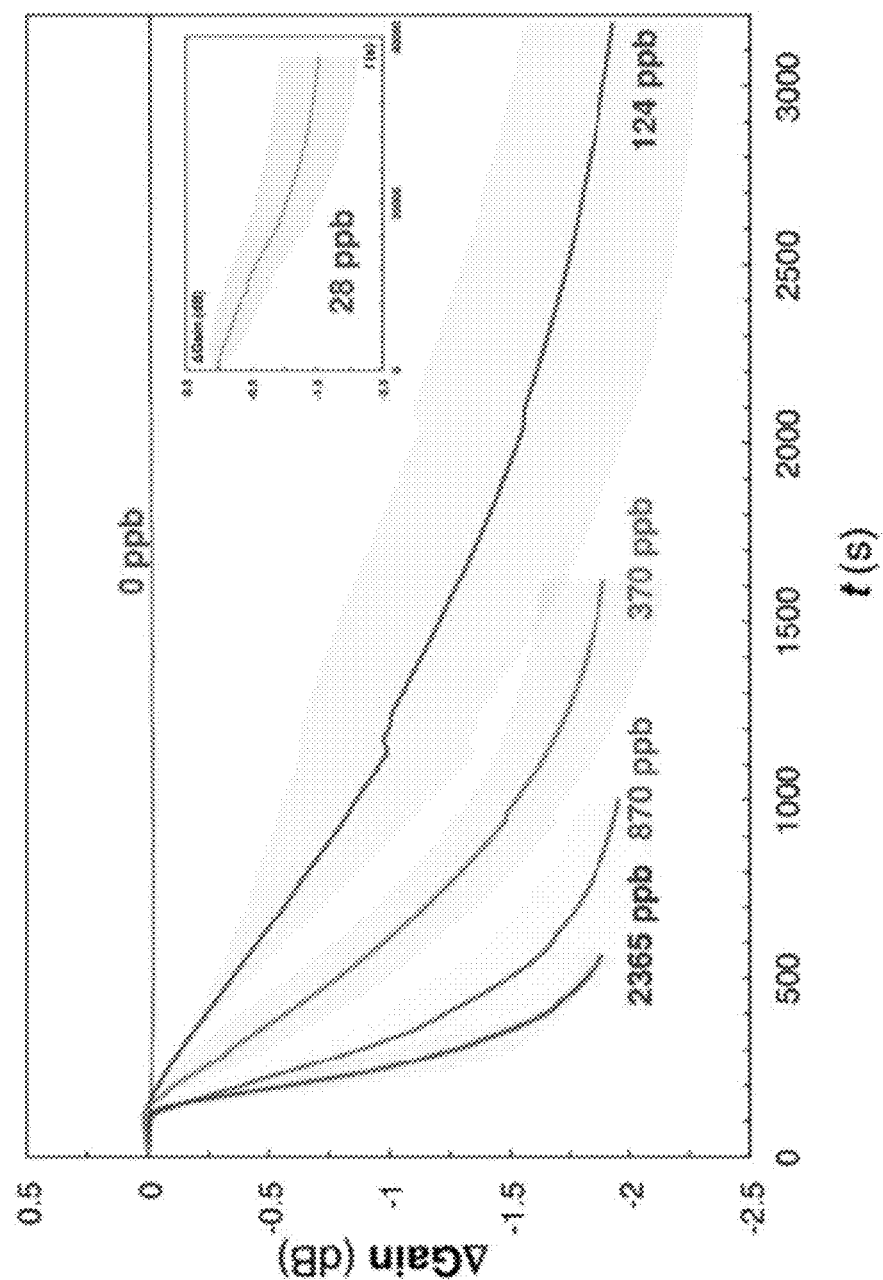
FIGS. 4A-4B show p-CARD DCP dosimeter performance with varying DCP concentrations.

With the optimized system in hand, its performance was evaluated toward various concentrations of DCP. A series of p-CARDs incorporated the BMIMCl/HFIPN/SWCNT-based chemiresistor. The individual device was exposed to a nitrogen flow for 100 s followed by DCP vapor until its gain readout reached saturation. The results are summarized in FIG. 4A. DCP exposure started at 100 s. The results are the averages of multiple individual devices tested (X=5, except for [DCP]=28 ppb where X=3 (inset)). Shaded areas indicate standard deviations.

Figure 4B:
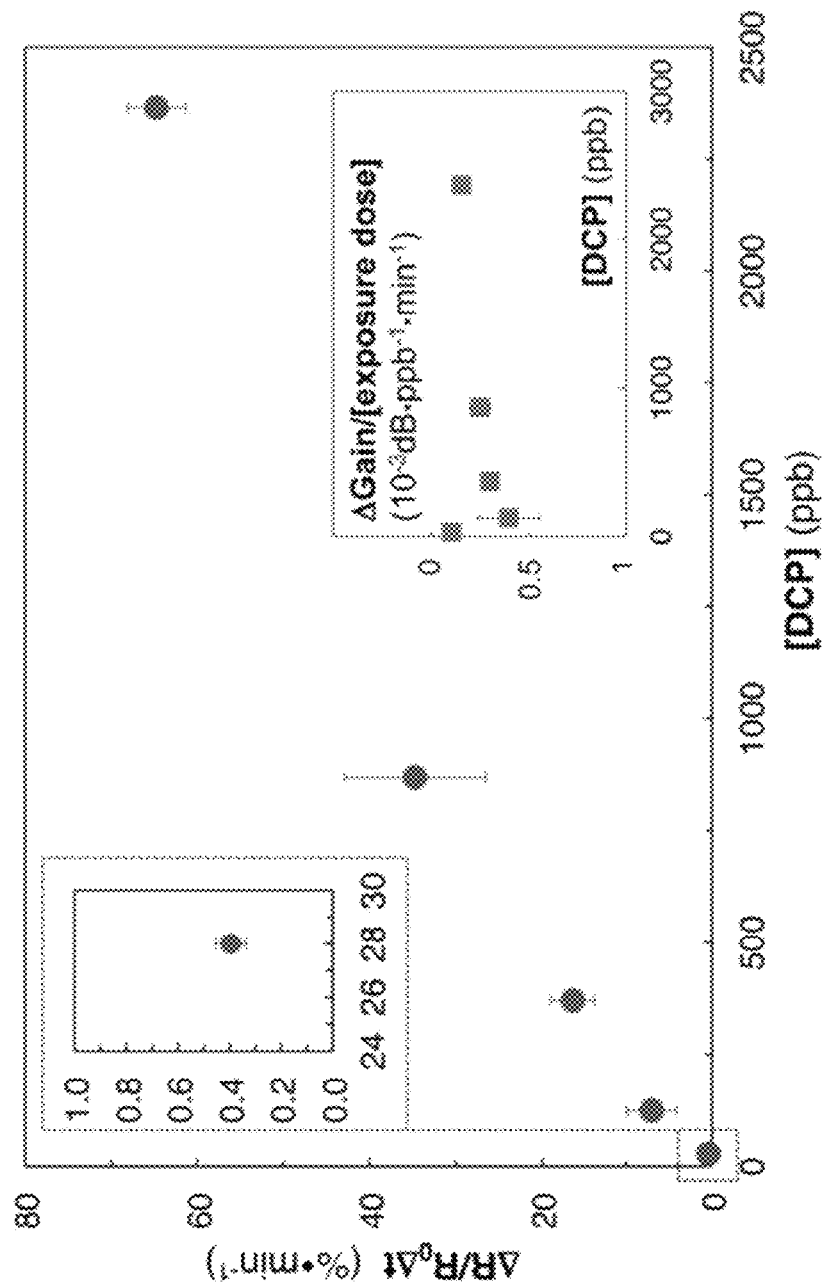

Consistent magnitudes of saturation response were observed ($\Delta$Gain~−1.9 dB, or $\Delta R/R_0$~1400%) when DCP concentration was larger than 100 parts-per-billion (ppb), while a slightly diminished overall change in gain was obtained with 28 ppb DCP ($\Delta$Gain~−1.5 dB). From the linear region of the saturation plots, the relative sensor resistance change per minute was extracted as a benchmark for detection sensitivity evaluation (FIG. 4B). The upper inset of FIG. 4B shows the zoom-in for [DCP]=28 ppb. The lower inset shows the exposure dose-normalized response determined for p-CARDs at each concentration tested. It was found that $R_s$ increased by over 60% after exposure to 2.4 ppm DCP for only 1 min. This high sensitivity and fast response kinetics allowed the detection of DCP at a concentration as low as 28 ppb, at a practical time scale (0.4%/min).

A true test of a dosimeter is based on the response behavior across all combinations of time and concentration. Ideally the response of a dosimeter is proportional to the exposure dose, the product of analyte concentration, and exposure time ([analyte]·$\Delta$t). It was determined across three orders of concentration magnitude that the exposure dose-normalized response (gain) of all p-CARDs tested fell within a relatively narrow range (FIG. 4B, lower inset), indicating concentration-independent dosimetry of the optimized system. By taking the average exposure dose normalized response, the exposure dose dependent relationship to the change in gain of a p-CARD can be empirically derived as:

$$\Delta \text{Gain} = A \int_{t_i}^{t_j} |DCP| dt \quad (1)$$

Where $A=-(2.5\pm1.2)\times10^{-4}$ dB~ppb$^{-1}$·min$^{-1}$ and t is in minutes. This key relationship thus enables unambiguous equivalent exposure assessments based on the relative change in gain. Furthermore, when combined with knowledge of the power-threshold of binary p-CARDs, pre-programmed p-CARDs that switch on and off after passing a pre-defined equivalent exposure threshold can be easily and predictably fabricated.

Figure 5:
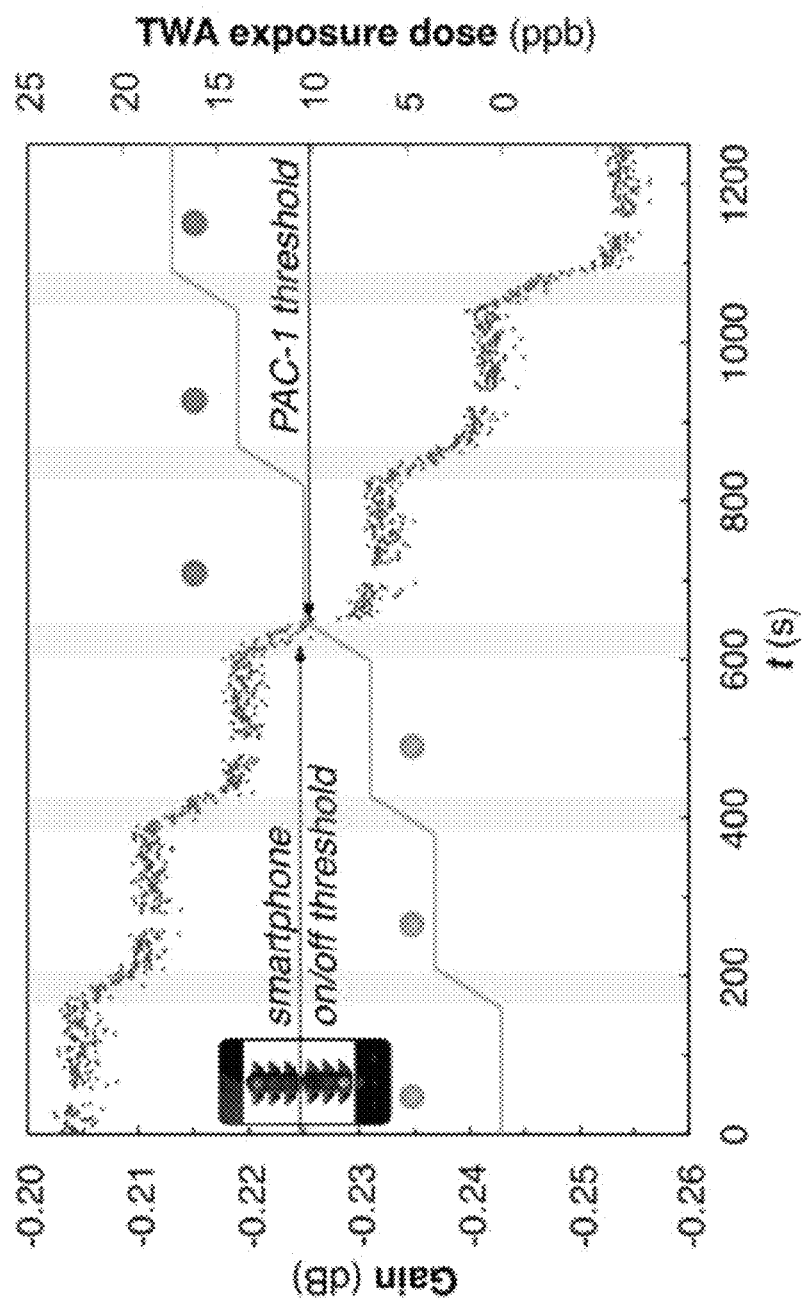
FIG. 5 shows p-CARD DCP PAC-1 dosimeter.
Figure 16:
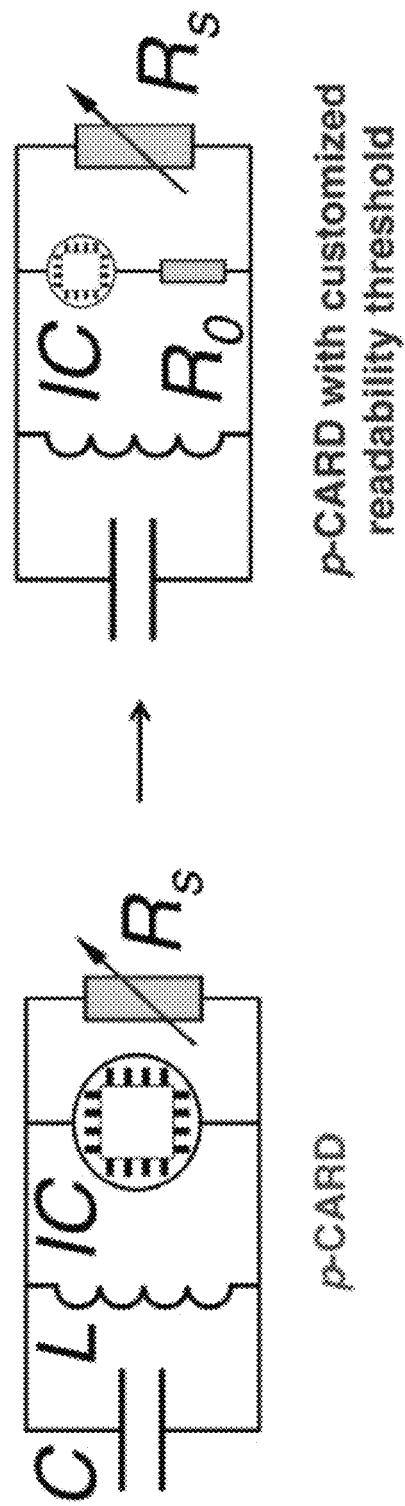
FIG. 16 shows circuit diagrams for p-CARD threshold customization.

The integrated circuit (IC) of a p-CARD can be designed to activate at a specific threshold by incorporation of a fixed resistor in series with the IC (FIG. 16). The ability to modify the IC activation threshold in this straightforward fashion allows the practitioner to tune the p-CARD to activate at pre-determined chemical concentration or chemical dose thresholds. This is reduced to practice in FIG. 5, wherein the practitioners designed a p-CARD to activate at a pre-determined chemical dose. FIG. 5 shows that the NA simulant-triggered smartphone binary switch of this system was demonstrated wherein a p-CARD was repeatedly exposed to DCP vapor (2 ppm) for 50 s followed by 170 s $N_2$. In FIG. 5, a p-CARD's gain (left axis, blue points) was measured while it was iteratively exposed to DCP (2 ppm in N2) (shaded bars). The equivalent exposure TWA (right axis, blue line) was calculated, and the p-CARD was addressed with a smartphone once per cycle. Below the PAC-1 threshold, p-CARD is unreadable (green dots). Above the PAC-1 threshold, the p-CARD becomes readable (red dots). The device was programmed to switch on when it had exceeded a PAC-1 threshold. Initially, p-CARD was below the smartphone's on/off threshold at gain=−0.225 dB, and thus was unreadable ("off" state, indicated by green dots). The corresponding frequency-gain plot of this device (t=0 s) was nearly flat, illustrating poor device resonance within the NFC reader's working frequency region (FIG. 16).

As the device was iteratively subjected to the DCP: 1) consistent irreversible gain readout decrease (R increase) was observed, as showcased by the staircase-shape plot; 2) the device's resonance amplitude increased, as indicated by the increasing depth of the minima in the frequency-gain plot; 3) After 3 cycles, corresponding to a PAC-1 TWA of 10 ppb, the device's resonance amplitude exceeded the readability threshold and became readable by the smartphone (state "on", indicated by red dots). While the binary switch with the commercial NFC tags has a threshold around −0.2 dB, a simple method was devised to customize this parameter.

Figures 6A, 6B:
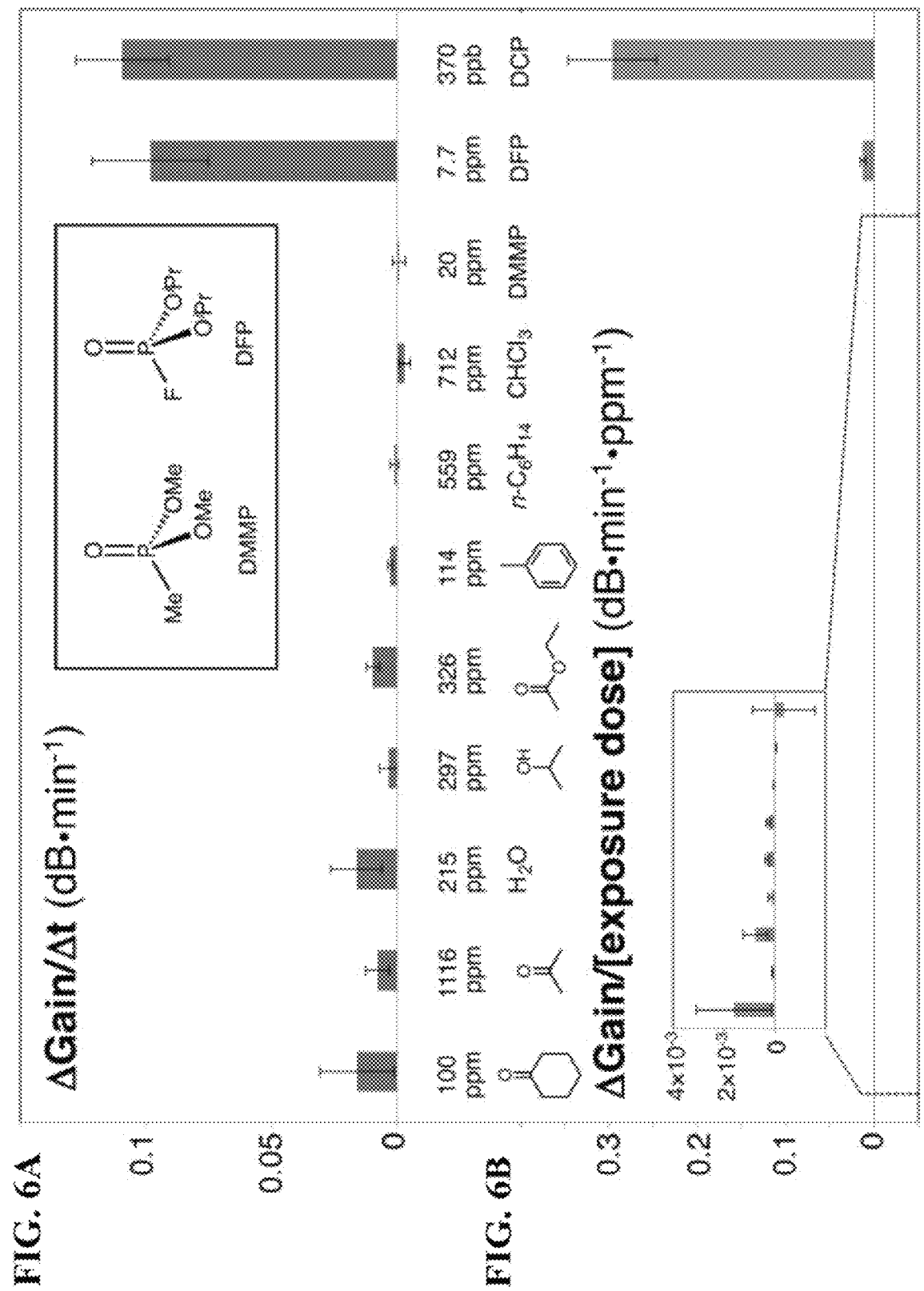
FIGS. 6A-6B show selectivity of p-CARD DCP dosimeter towards interferents. Change in p-CARD gain as a function of (a) exposure time (FIG. 6A) and (b) exposure dose (FIG. 6B).

When it comes to in-field chemical hazard dosimetry, chemiresistor selectivity to the target analyte over commonly encountered interferent chemicals is critical for minimizing the occurrence of false alarms. See, Y. Seto, M. Kanamori-Kataoka, K. Tsuge, I. Ohsawa, K. Matsushita, H. Sekiguchi, T. Itoi, K. lura, Y. Sano, S. Yamashiro, *Sens. Actuators B-Chem.* 2005, 108, 193-197, which is incorporated by reference in its entirety. Toward this end, a series of potential interferent chemicals were evaluated. Overall, the responses ($\Delta$Gain/$\Delta$t) of the p-CARD DCP dosimeter toward NA simulants (DCP and diisopropyl fluorophosphate, DFP) at ppb or low-ppm level were at least one order of magnitude larger than those resulted from the highly concentrated interferent vapors (100 ppm~1000 ppm) (FIG. 6A). This good selectivity can be better characterized by the exposure dose-normalized responses (FIG. 6B). Among the interferents tested, ketone, ester, or hydroxyl functional group containing compounds afforded detectable sensor resistance increase, presumably via hydrogen-bonding. Hydrocarbon/halogenated hydrocarbons were essentially inert to the sensor. Ammonia vapor led to sensor resistance decrease, which is likely due to a deprotonation process. Dimethyl methylphosphonate (DMMP), a hydrogen-bond accepting NA simulant that does not react covalently under these conditions, elicited a much smaller response than DCP and DFP at comparable concentrations, which is consistent with the irreversible hydrolysis proposed for the response to DCP and DFP. p-CARDs did not respond significantly to low concentrations of water vapor (<10% relative humidity) and the response to DCP was not significantly affected under such level of humidity. However, a continuous flow (0.5~1.5 L/min) of moisture vapor of elevated humidity (30% to 100% of the saturation humidity) could compromise the sensor.

In conclusion, a highly sensitive and selective disposable wireless dosimetric chemical hazard badge can reliably detect NA simulants down to 28 ppb. This badge allows the quantification of chemical hazard dose in a temporally correlated fashion and transmission of that information wirelessly, enabling real-time hazard assessment that is relevant to widely employed chemical hazard regulation standards.

EXAMPLES

General Materials

All chemicals were used as received, except diethyl chlorophosphate. Diethyl chlorophosphate (DCP) and diisopropyl fluorophosphate (DFP) are powerful cholinesterase inhibitors and should be treated with great care and respect. All experiments were conducted in a fume hood with appropriate safety equipment and safety measures, including chemical goggles, long-sleeved chemically resistant lab coat, and gloves (nitrile and SilverShield®). In addition to conducting all handling of DCP and DFP in a well ventilated fume hood, a canister gas mask was used any time an open container was being handled. A bath of aqueous sodium hydroxide (NaOH) was kept at the ready, and any glass, syringes, needles, or other apparatus that came in contact with DCP or DFP were immersed in the solution and allowed to soak for several days prior to submission to appropriate waste streams. Anyone attempting to reproduce the experiments reported herein should consult the respective material safety data sheets (MSDS) and other pertinent safety information and understand the risks involved in handling cholinesterase inhibitors such as DCP and DFP. SWCNTs (purified≥95% as SWCNT) were kindly provided by Nano-C, Inc. (Westwood, MA). 2-(2-Hydroxy-1,1,1,3,3,3-hexafluoropropyl)-1-naphthol (CAS: 2092-87-7) was purchased from Santa Cruz Biotechnology (Dallas, TX). 1-n-butyl-3-methylimidazolium chloride (CAS: 79917-90-1) (BMIMCl) and diethylchlorophosphate (CAS: 814-49-3) (DCP) was purchased from Alfa Aesar (Heysham, Lancashire, UK). DCP was stirred vigorously over poly-4-vinylpyridine (P4VP) with active nitrogen flow for 24 hours prior to use in sensing experiments to reduce in situ hydrochloric acid. DCP was stirred vigorously over P4VP for the duration of all experiments. Poly-4-vinylpyridine (Mw~200, 000) (CAS: 25232-41-1), 1-Butyl-3-methylimidazolium hexafluorophosphate (CAS: 174501-64-5) (BMIMPF$_6$), cyclohexanone (CAS: 108-94-1), acetone (CAS: 67-64-1), isopropanol (CAS: 67-63-0), ethyl acetate (CAS: 141-78-6), toluene (CAS: 108-88-3), n-hexane (CAS: 110-54-3), chloroform (CAS: 67-66-3), dimethyl methylphosphonate (CAS: 756-79-6) (DMMP), and diisopropyl fluorophosphate (CAS: 55-91-4) (DFP) were purchased from Sigma-Aldrich (St. Louis, MO). CD3CN (2206-26-0) was purchased from Cambridge Isotope Laborotories, Inc.

Sensing Enclosure

All near field communication (NFC) tags used in this study (hereafter referred to generically as "NFC tag") were Texas Instruments HF-I Tag-It 13.56 MHz RFID transponder square in-lays (MFG: RI-I11-114A-01), purchased from DigiKey (Thief River Falls, MN).

Figure 11:
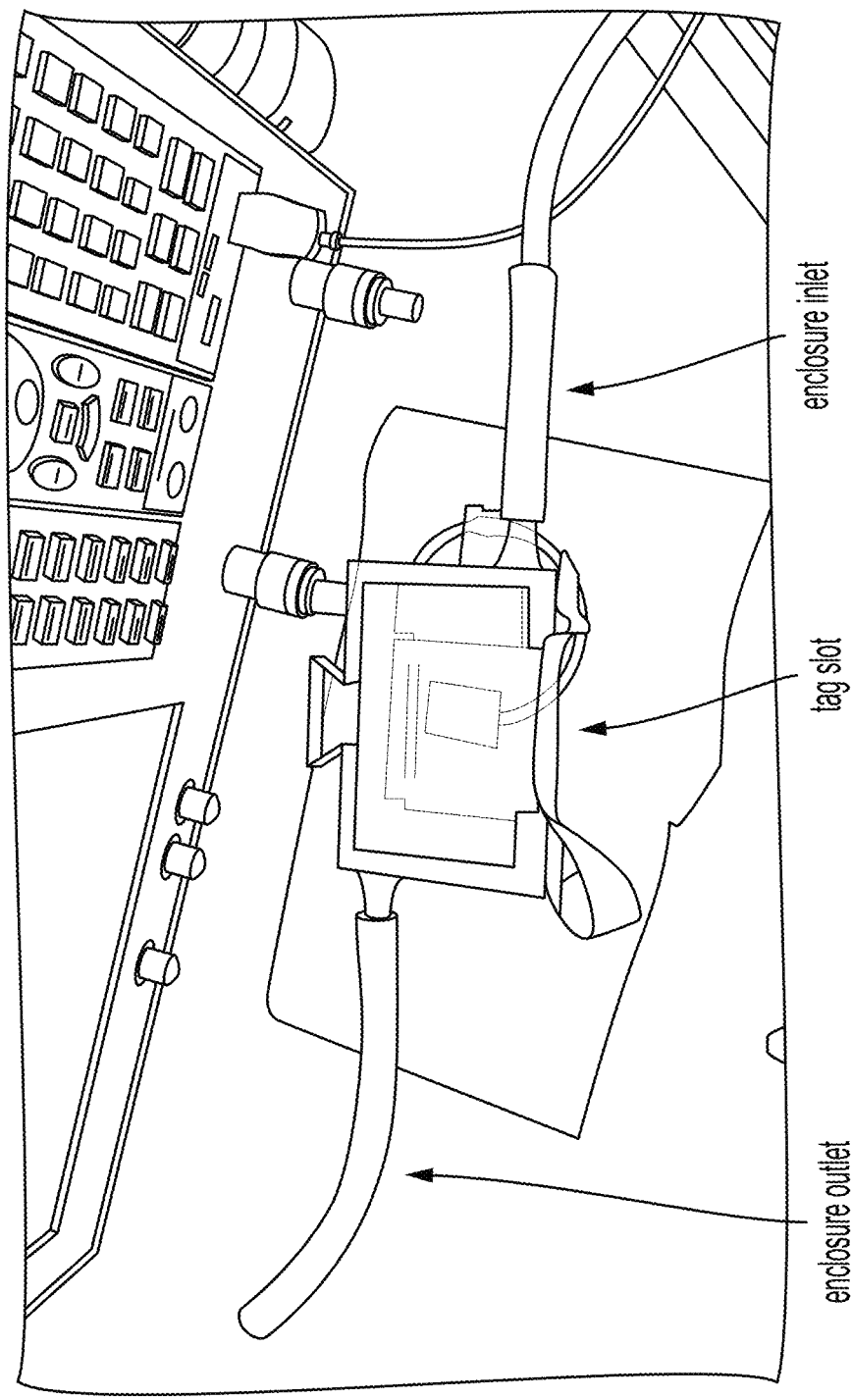
FIG. 11 shows sensing enclosure.
Figure 12A:
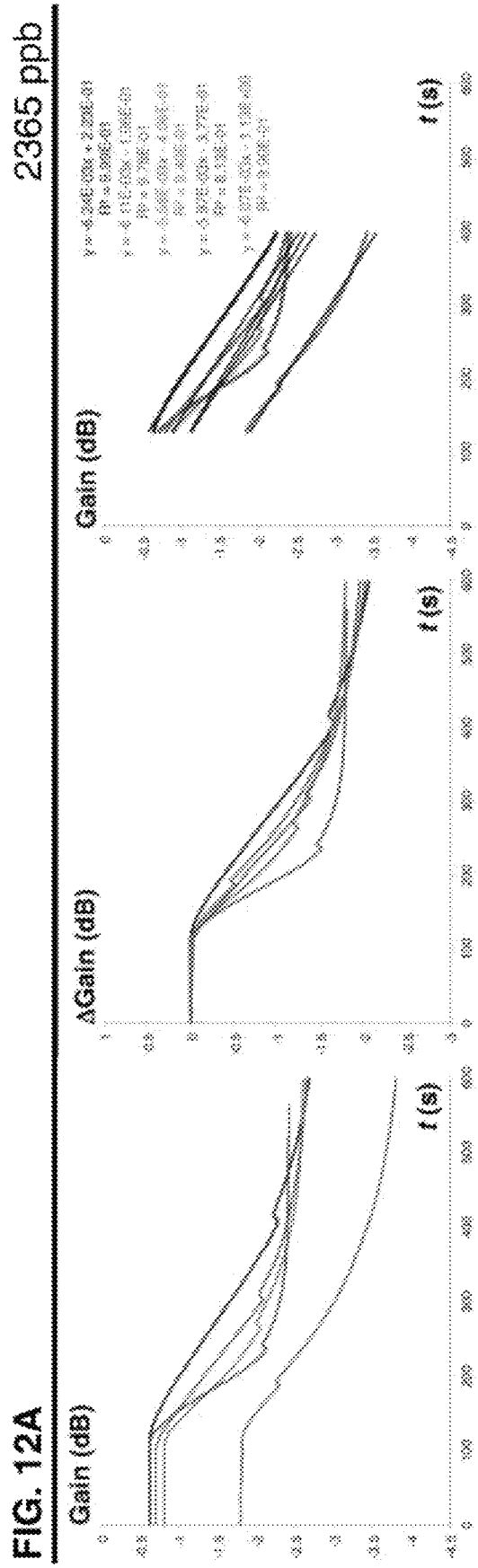
FIGS. 12A-12E show DCP saturation exposure experiments of p-CARDs at (a) 2365 ppb, (b) 870 ppb, (c) 370 ppb, (d) 124 ppb, (e) 28 ppb.
Figure 12B:
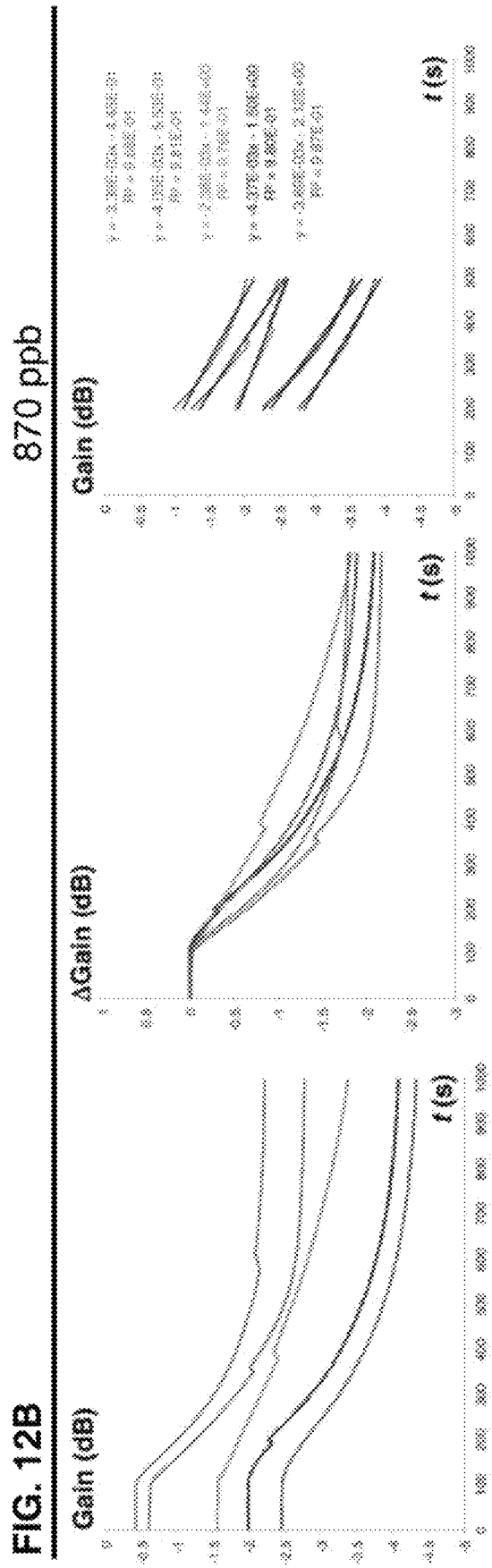
Figures 12C, 12D:
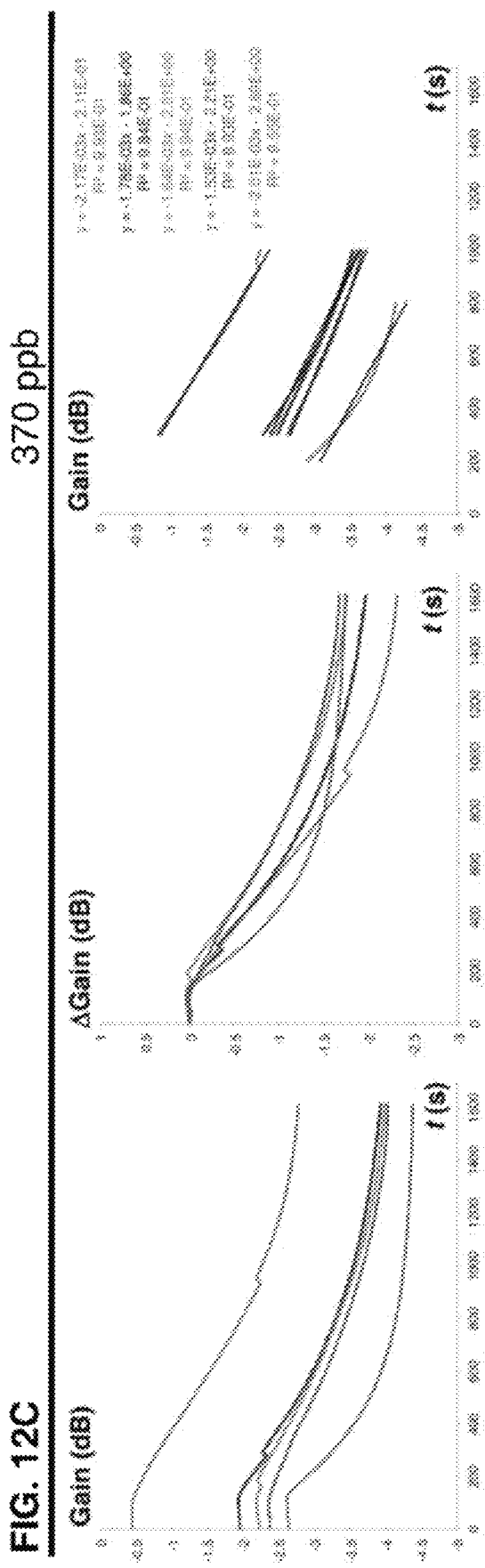
Figure 12E:
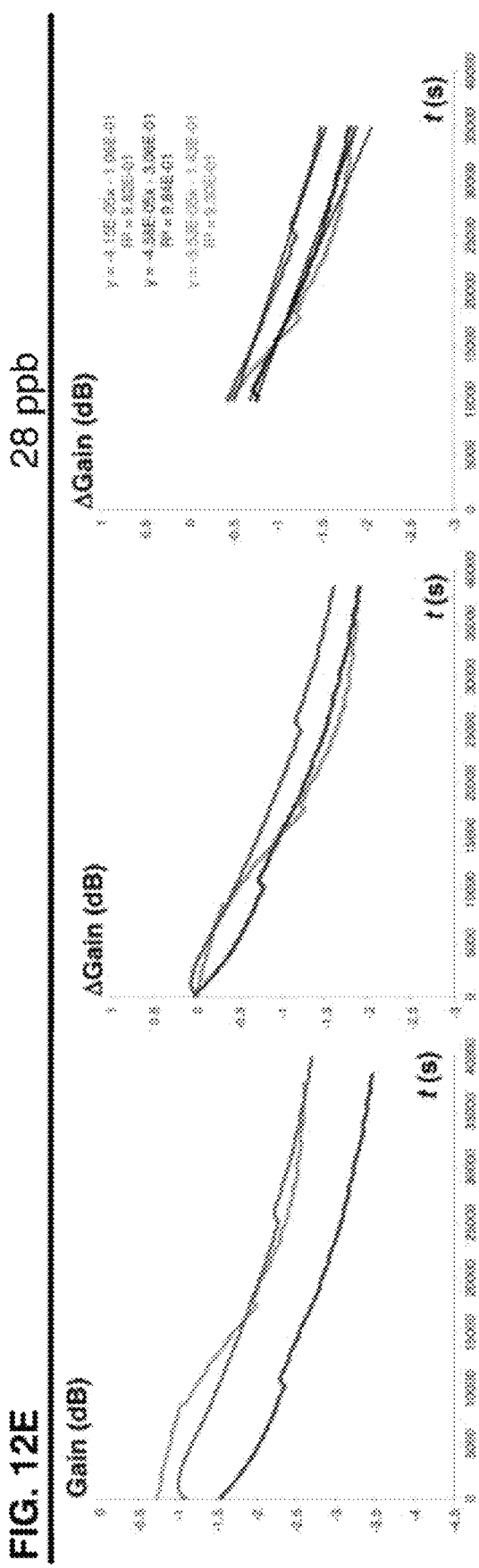
Figure 13:
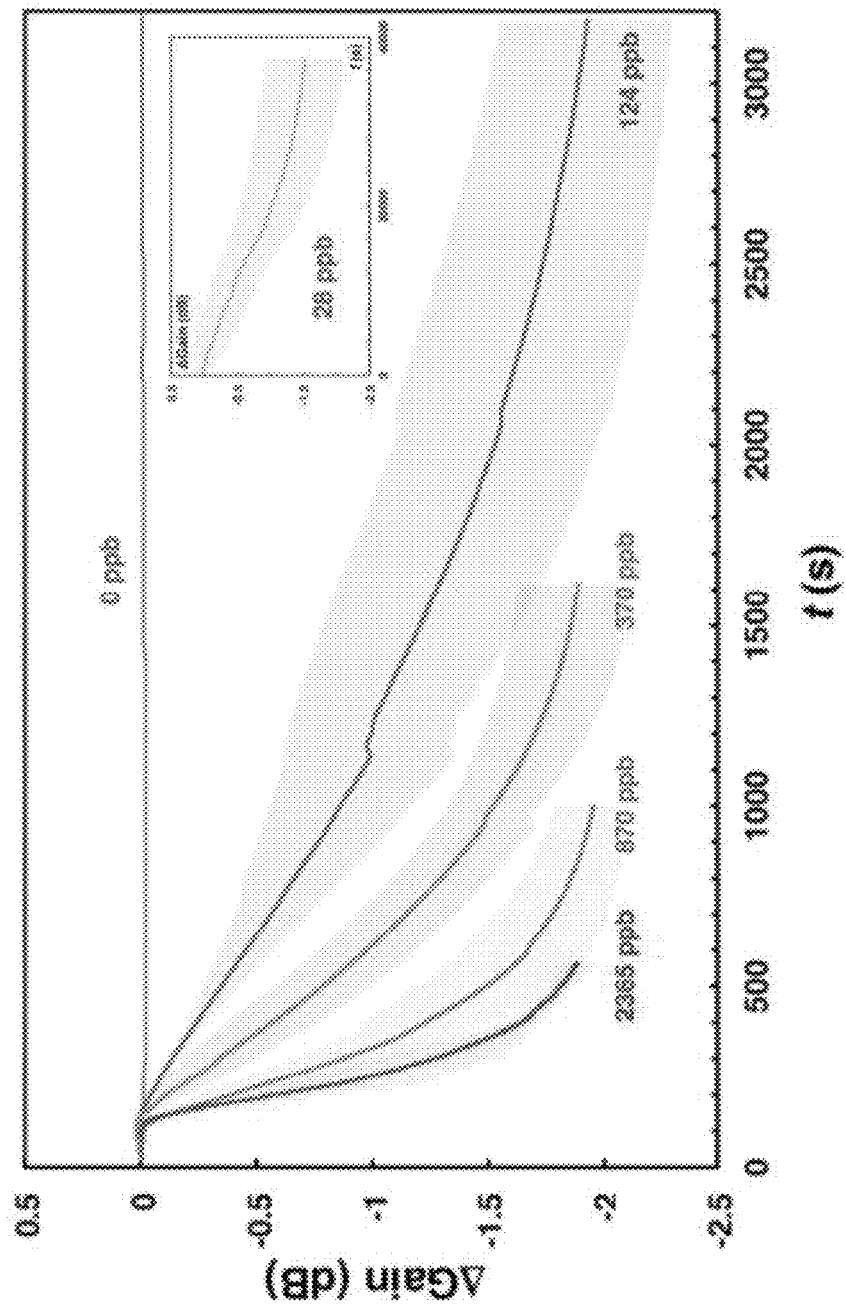
FIG. 13 shows summary of p-CARD saturation plots. Shaded areas indicate standard deviations.

A sensing enclosure was fabricated with a ProJet® 6000 3D printer (3D Systems, Andover, MA). The enclosure comprises of an inlet, outlet, and CARD receptacle (FIG. 11). The receptacle opening can be closed off with electrical tape or putty prior to use.

Choice of Tags

This study uses commercially available Texas Instruments HF-I Tag-It Plus Transponder Inlays (TI-Tag) to demonstrate the concept of converting a commercially available NFC tag into a chemical dosimeter. These tags were chosen based on their chemically robust substrate, absence of protective polymeric coating over the circuitry, commercial availability, and low cost. The electronic circuitry of the unmodified tags is supported via polyurethane glue on both sides of a thin (47 µm), flexible sheet of polyethylene terephthalate, which also serves as a dielectric layer for the tuning capacitor.

Choice of Analytes

A wireless hazard badge's utility is dependent upon its selectivity in responding to the target chemical hazard over other analytes. The method disclosed herein does not employ data analysis or computationally-intensive interpretation. The selective detection of DCP over other analytes can be probable concern in a broad array of contexts, including agricultural and military settings. Cyclohexanone is a known solvent used in the recrystallization of explosives. See, H. Lai, A. Leung, M. Magee, J. R. Almirall *Anal. Bioanal. Chem.* 2010, 396, 2997-3007, which is incorporated by reference in its entirety. Acetone is a commonly encountered solvent present in pure form as well as a component of consumer products and commercial formulations. Water vapor is present in many indoor and outdoor scenarios and products. Isopropanol is a commonly employed cleaner and industrial solvent. Ethyl acetate is used in a number of commercial and consumer products. Toluene was employed as a simulant of benzene, xylenes, and polyaromatic hydrocarbons (PAHs), which are present in fuels (i.e. gasoline, diesel, etc.), cigarette smoke, and combustion products (i.e. exhaust gases). See, A. H. Miguel, T. W. Kirchstetter, R. A. Harley, S. V. Hering, *Environ. Sci. Technol.* 1998, 32, 450-455, which is incorporated by reference in its entirety. Hexane was employed as an analog of saturated hydrocarbons, used as industrial solvents as well as to simulate petroleum fuels (i.e. gasoline and diesel). Chloroform is a commonly encountered organic solvent. Dimethyl methylphosphonate (DMMP) is a non-reactive phosphonate. Diisopropyl fluorophosphonate (DFP) is a nerve agent simulant that is of close chemical relation to the 'real' chemical warfare agents sarin, soman, and cyclosarin. See, H. P. Benschop, L. P. A. De Jong, *Acc. Chem. Res.* 1988, 21, 368-374, which is incorporated by reference in its entirety. In addition to their relevance as potential interferents and alternative nerve agent simulants, each analyte was tested to define the functional group reactivity space of the optimized nerve agent hazard badges.

Choice of Smartphone

The Samsung Galaxy™ S4 (SGS4) was utilized to demonstrate wireless chemical dosimetry for two reasons: (i) the Samsung's Galaxy series are amongst the most widely distributed "smart" mobile devices in history; (ii) the SGS4 runs on Android, one of the most widely distributed operating systems that supports NFC applications. Previously, we've demonstrated wireless chemical sensing via NFC with other smartphone models. The smartphone-embedded NFC chip comprises an antenna for inductive coupling with NFC tags, a transmission module with microcontroller for 13.56 MHz carrier signal generation and tag signal demodulation, as well as embedded and external (Subscriber Identity Module (SIM) card) security elements. When used with unmodified TI-tags, the SGS4 can read tags at ~5 cm standoff distance through solid, non-metallic objects such as paper, plastic, and liquids. See, J. M. Azzarelli, K. A. Mirica, J. B. Ravnsbæk, T. M. Swager, *Proc. Natl. Acad. Sci.* 2014, 111, 18162-18166, which is incorporated by reference in its entirety.

Choice of Smartphone Application

The 'NFC Reader' (Adam Nybäck; 5 Jul. 2013) was used to read the tags, and is freely available from the Google Play™ Store at the time of this report. This application was chosen because it displays the tag's unique identification number without invoking other time- or energy-intensive functions of the smartphone. For the purposes of this study, the tag is considered "on" or "readable" if the unique identification number can be retrieved within 5 seconds or less of holding the smartphone at ~2.5 cm distance away from the tag. Conversely, the tag is considered "off" or "unreadable" if the unique identification number cannot be retrieved under the same conditions.

Dilution of Vapors

Figure 8:
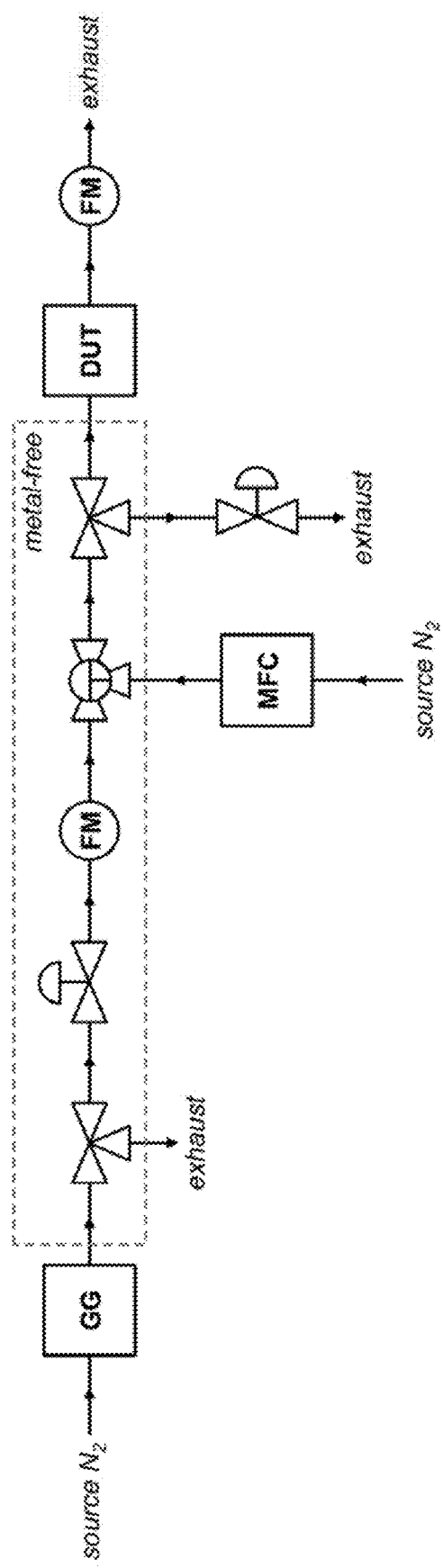
FIG. 8 shows vapor delivery setup.
Figure 9:
FIG. 9 shows p-CARD fabrication: dropcast location.

Delivery of controlled concentrations of vapors to devices was carried out using FlexStream™ Gas Standards Generator Model FlexBase (Kin-Tek Laboratories, La Marque, TX). All vapors were diluted with nitrogen ($N_2$) at total flow rates of 0.25-1.00 L/min. Further dilution of vapor streams delivered to devices was performed using MC Standard Series Mass Flow Controller, model MC-10SLPM-D/5M (Alicat Scientific, Tuscon, AZ) total flow rates of 1 L/min. The general vapor delivery setup is illustrated in FIG. 8.

Dispersion of SWCNTs

To a vial charged with SWCNTs (0.25 mg), BMIMCl (10 mg) and HFIPN (3.0 mg) was added o-dichlorobenzene (1.8 mL) and dimethylformamide (0.20 mL). The resulting mixture (A) was sonicated at ambient temperature for 10 min before use.

Fabrication of p-CARDs p-CARDs were fabricated by dropcasting 'A' (1 µL) at the location indicated in Figure S1, followed immediately by solvent removal by subjecting the device to a high vacuum environment in a vacuum desiccator for 10 minutes. This process was repeated (in total 2 µL A was employed). Finally, the p-CARDs were allowed to sit under ambient atmosphere for 12-24 hours before being tested or characterized.

Device RF Response Characterization and Data Acquisition

The RF signal response of the modified NFC tags was monitored from 10-20 MHz with a custom-made loop probe connected via a BNC cable to a vector network analyzer (VNA) (Agilent E5061B) by measuring reflection coefficient ($S_{11}$) at 50Ω port impedance and 0 dBm input power. The $S_{11}$-determined resonant frequency ($f_0$) minimum gain value (dB) was measured and acquired using a custom-built LabView program (Marshall Craft, MIT) that executed a minimum-search algorithm at specified time intervals and tabulated the data into an exportable comma separated value (.csv) file. Microsoft Excel was used to calculate change in gain, relative change in resistance, and change in gain per exposure dose.

Correlating p- and s-CARD Gain with $R_s$

A series of modified NFC tags, each with a different fixed resistor ($R_{fixed}$) were built in the p- and s-CARD architecture (FIG. 10A). Conceptually, it is assumed that because the SWCNTs used in this study are predominantly semi-conducting, $R_{fixed}$ is a reasonable approximation for $R_s$. The fixed-resistor-NFC tags' RF response characterized according to the method described above and their respective $f_0$ minimum gain values were recorded. Gain values are then plotted as a function of $\log(R_s)$ (FIG. 10B), from which the relationship between gain and $R_s$ was empirically derived (FIG. 10C).

p-CARD Gas Sensing Experiments: General Design p-CARD response to gas exposure was determined accordingly: a p-CARD was placed in the sensing enclosure, and the enclosure was sealed with electrical tape (FIG. 11). House-supplied nitrogen was delivered to the p-CARD via the enclosure inlet for a pre-determined period of time (typically between 200 s-1200 s). Then, the p-CARD was exposed to the analyte of interest at a known concentration; depending on the experiment, the duration of exposure was either for a pre-determined period of time, or until the device response 'saturated' (i.e. as $(\text{gain}_n\text{-gain}_{n-1})/\text{gain}_{n-1}$ approaches zero). Following analyte exposure, the p-CARD was exposed to house-supplied nitrogen for a pre-determined period of time (typically 200 s-1200 s).

DCP Saturation Experiments and Correlating $\Delta\text{gain}/\Delta t$ and $\Delta R/R_0 \Delta t$ Following the procedure described in the general design of p-CARDs sensing experiments, a p-CARD was first exposed to 100 s pure $N_2$, followed by x ppb DCP vapor until the device response saturated (x=28, 124, 370, 870, 2365; FIGS. 12A-12E and 13). The device was continuously monitored by a VNA. For each concentration, five individual p-CARDs were tested (except for 28 ppb where three were tested). Based on eq. S2, time-normalized relative resistance change $\Delta R/R_0 \Delta t$ was calculated using the following formula (Table 1, FIG. 13):

$$\Delta \text{Gain} = -1.66 lg\left(\frac{R}{R_0}\right) \quad \text{(eq. S2)}$$

$$\frac{\Delta R}{R_0 \Delta t} = \left(10^{\left(\frac{\Delta \text{Gain}}{\Delta t} \cdot \frac{60}{(-1.66)}\right)} - 1\right) \cdot 100\% \quad \text{(eq. S3)}$$

TABLE 1

Calculations of time-normalized relative resistance change.

| DCP concentration (ppb) | ΔGain/Δt (dB/min) | ΔGain/Δt* [DCP] (dB/ppb*min) | Average ΔGain/Δt* [DCP] (dB/ppb*min) | Std ΔGain/Δt* [DCP] (dB/ppb*min) |
|---|---|---|---|---|
| 28 | −2.49E−03 | −8.89E−05 | −1.02E−04 | 1.51E−05 |
|  | −2.75E−03 | −9.81E−05 |  |  |
|  | −3.32E−03 | −1.19E−04 |  |  |
| 124 | −2.53E−02 | −2.04E−04 | −3.91E−04 | 1.55E−04 |
|  | −4.12E−02 | −3.32E−04 |  |  |
|  | −4.10E−02 | −3.30E−04 |  |  |
|  | −5.99E−02 | −4.83E−04 |  |  |
|  | −7.50E−02 | −6.05E−04 |  |  |
| 370 | −1.30E−01 | −3.52E−04 | −2.96E−04 | 4.26E−05 |
|  | −1.07E−01 | −2.89E−04 |  |  |
|  | −9.84E−02 | −2.66E−04 |  |  |
|  | −9.18E−02 | −2.48E−04 |  |  |
|  | −1.21E−01 | −3.26E−04 |  |  |

TABLE 1-continued

Calculations of time-normalized relative resistance change.

| | | | | |
|---|---|---|---|---|
| 870 | −1.43E−01 | −1.64E−04 | −2.46E−04 | 5.16E−05 |
| | −2.21E−01 | −2.54E−04 | | |
| | −2.59E−01 | −2.97E−04 | | |
| | −2.03E−01 | −2.34E−04 | | |
| | −2.43E−01 | −2.79E−04 | | |
| 2365 | −3.74E−01 | −1.58E−04 | −1.52E−04 | 6.36E−06 |
| | −3.67E−01 | −1.55E−04 | | |
| | −3.35E−01 | −1.42E−04 | | |
| | −3.59E−01 | −1.52E−04 | | |
| | −3.64E−01 | −1.54E−04 | | |

| DCP concentration (ppb) | $\Delta R/R_0 \Delta t$ (%/min) | Average $\Delta R/R_0 \Delta t$ (%/min) | Std $\Delta R/R_0 \Delta t$ (%/min) |
|---|---|---|---|
| 28 | 0.346 | 0.396 | 0.059 |
| | 0.382 | | |
| | 0.461 | | |
| 124 | 3.57 | 7 | 2.9 |
| | 5.88 | | |
| | 5.85 | | |
| | 8.67 | | |
| | 11 | | |
| 370 | 19.8 | 16.4 | 2.6 |
| | 16 | | |
| | 14.6 | | |
| | 13.6 | | |
| | 18.2 | | |
| 870 | 21.9 | 34.7 | 8.2 |
| | 35.9 | | |
| | 43.1 | | |
| | 32.6 | | |
| | 40.1 | | |
| 2365 | 68.1 | 64.7 | 3.4 |
| | 66.3 | | |
| | 59.2 | | |
| | 64.4 | | |
| | 65.7 | | |

Scanning Electron Microscopy and Optical Microscopy

Scanning electron microscopy (SEM) was carried out using a JEOL JSM-6700F field emission SEM (FESEM). Typical accelerating voltages were 1.5-5.0 kV.

Optical microscope images were collected with a Leica DMRXP microscope (Buffalo Grove, IL) equipped with a CCD video camera (Sony Power HD, DXC-970 MD) using a 10× objective (FIG. 14).

Nuclear Magnetic Resonance Spectroscopy $^{31}$P NMR spectra were acquired on a Bruker Avance Spectrometer operating at 162.0 MHz and calibrated using 85% aqueous phosphoric acid as an external standard. NMR kinetics experiments (FIGS. 7A-7B):

Conditions A: A 5 mL vial equipped with a magnetic stir bar was charged with 100 mg BMIMCl, 5 mg HFIPN and 50 μL CD$_3$CN. The mixture was sonicated at r.t. for 5 min to afford a viscous solution. At r.t. upon stirring 10 μL DCP was added via syringe (t=0 s). A 20 μL aliquot of the mixture was taken at t=x s (x=30, 60, 180, 600), diluted with 0.5 mL CD$_3$CN and analyzed by NMR spectroscopy.

Conditions B: A 5 mL vial equipped with a magnetic stir bar was charged with 100 μL CD$_3$CN and 10 μL H$_2$O. At r.t. upon stirring 10 μL DCP was added via syringe (t=0 s). A 20 μL aliquot of the mixture was taken at t=x s (x=30, 60, 180, 600), diluted with 0.5 mL CD$_3$CN and analyzed by NMR spectroscopy.

Hazard Badge Dosimetry

Figure 15:
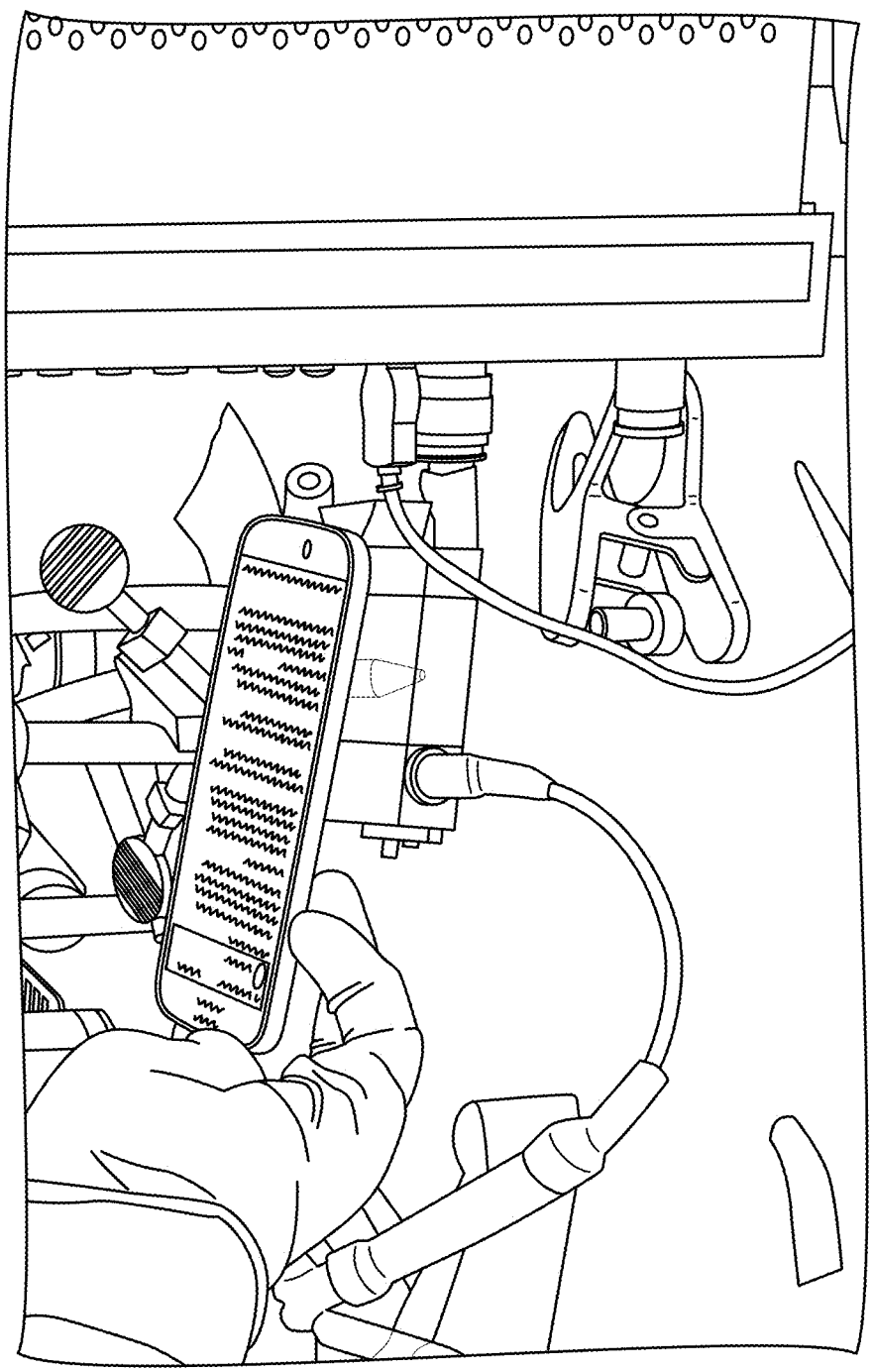
FIG. 15 shows SGS4 measurement of hazard badge during an experiment.

Following the procedure described in the general design of p-CARDS sensing experiments, a p-CARD went through a series of exposure cycles and was continuously monitored using a VNA. In each cycle, the p-CARD was first exposed to 50 s of 2 ppm DCP in N$_2$ followed by 170 s pure N$_2$. At the 100 s of each exposure cycle, the p-CARD was read by a SGS4 (×3) to determine its readability (OFF/unreadable or ON/readable) and then the corresponding resonance-frequency trace was captured. In each cycle all the three readability tests gave the same result (FIG. 15).

With the current experimental setup, p-CARDs derived from one-step modification of commercial NFC tags have a readability threshold around −0.2 dB. While these p-CARDs proved successful in smartphone binary switch experiments, methods that would allow one to customize the readability threshold of the device to adapt to different situations have not been developed. This can be achieved by the incorporation of an additional resistor ($R_0$) in series with the integrated circuit (IC), as illustrated in FIG. 16. By increasing the resistance of $R_0$, a customizable threshold can be obtained. For instance, modified p-CARDs had threshold around −0.4 dB using this method.

Interferent Testing

Figure 17:
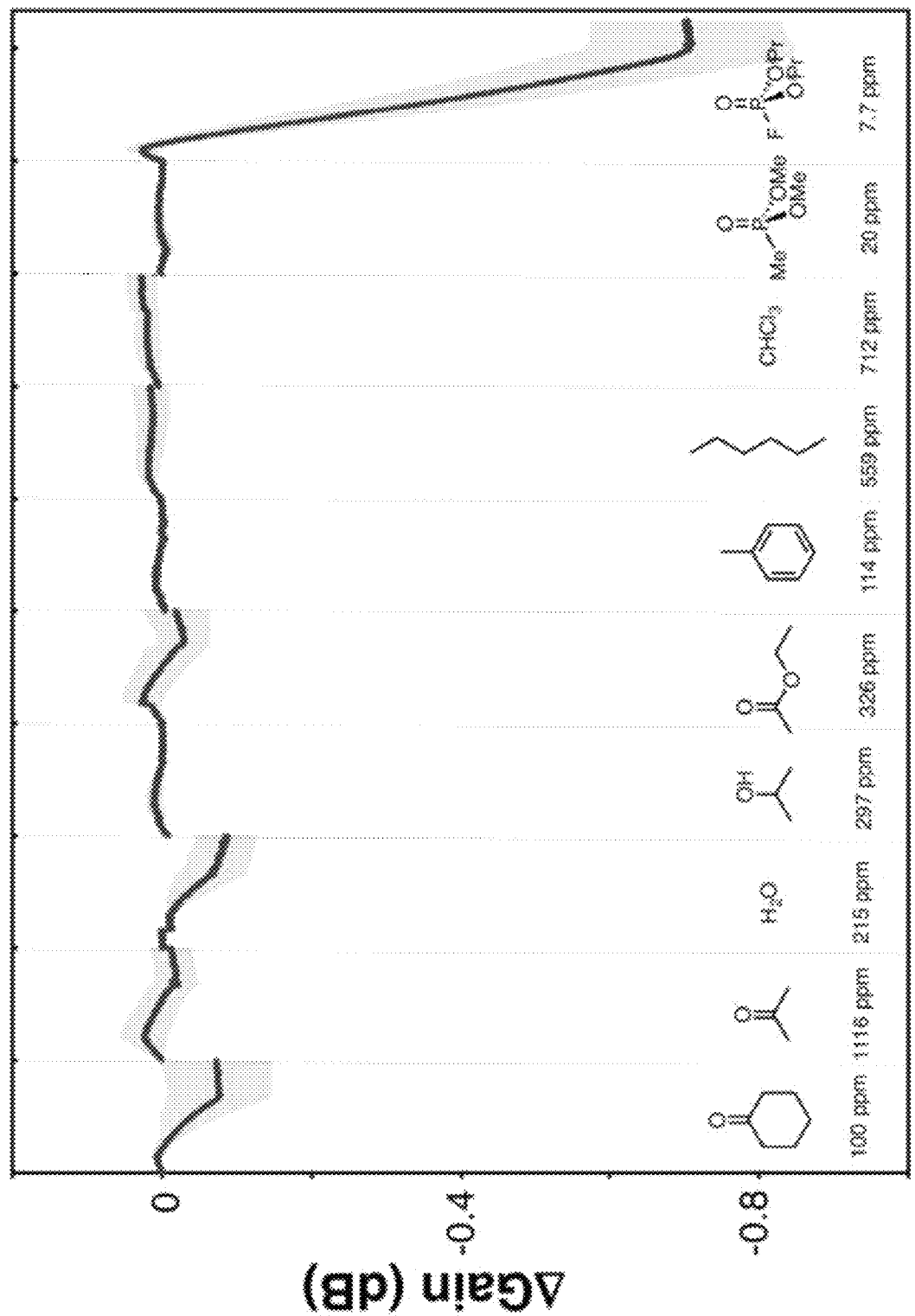
FIG. 17 shows interferent testing results.

Following the procedure described in the general design of p-CARDs sensing experiments, a p-CARD was first exposed to 100 s pure N$_2$, followed by 300 s exposure of the analyte vapor, and finally 200 s pure N$_2$ (except for DFP), while continuously monitored using a VNA. For DFP: 100 s pure N$_2$, followed by 500 s exposure of DFP vapor, and finally 200 s pure N$_2$ (FIG. 17). FIG. 17 shows relative change gain upon exposure of p-CARD to interferents (300 s, except DFP, 500 s). Average responses traces and standard deviation (shaded area; n=3, except DFP n=2). For water, isopropanol, hexane, chloroform and DMMP, baseline corrections were applied.

Humidity Tolerance Test:

p-CARDs did not respond significantly to low concentrations of water vapor (<10% relative humidity) and the response to DCP was not significantly affected under such level of humidity. This is consistent with the fact that the fabrication, maturing (12 h~1d) and storage (>3d) of these devices was performed under ambient conditions (typically 20%~50% relative humidity).

Figure 18:
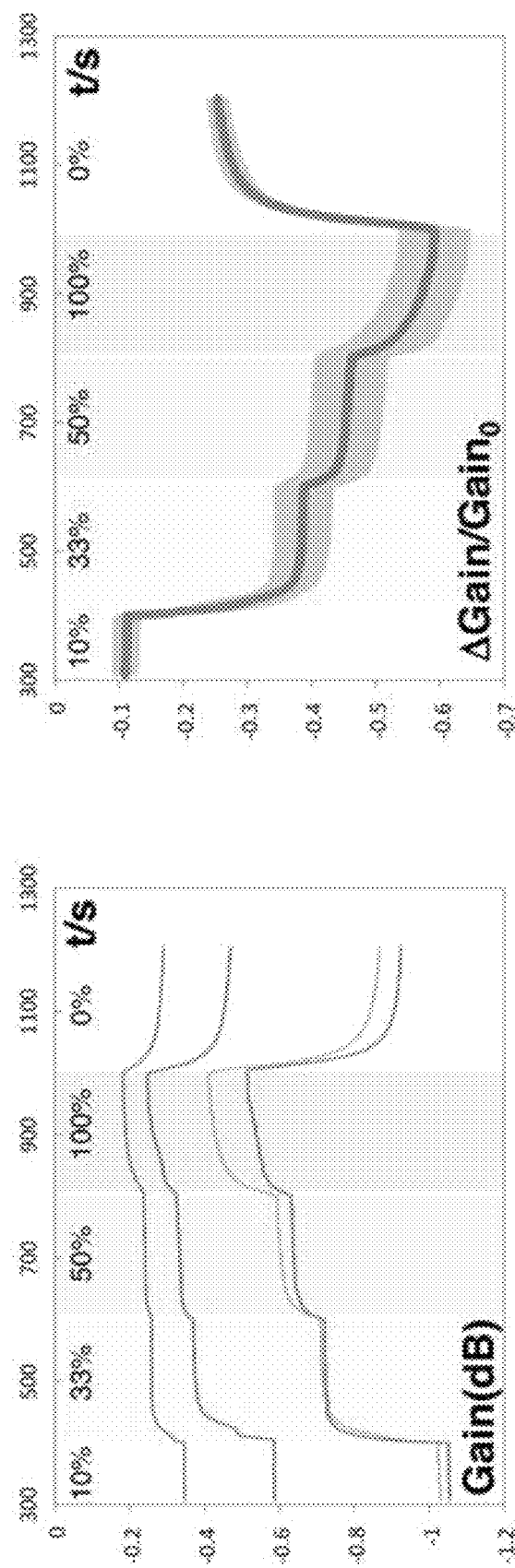
FIG. 18 shows p-CARD responses to a continuous flow of moisture vapor.

However, a continuous flow (0.5~1.5 L/min) of moisture vapor of elevated humidity (30% to 100% of the saturation humidity) resulted in significant responses in the device gain readout (FIG. 18). FIG. 18 shows p-CARD responses to a continuous flow (0.5~1.5 L/min) of moisture vapor (0%~100% of saturated vapor pressure, 23° C.). Left: gain traces of 4 individual devices. Right: average relative gain change based on initial gain. The shaded area indicates standard deviation.

This response to high content of water is very different from that to DCP in three aspects: (1) the device saturated at different levels under different humidity; (2) the response was largely reversible; (3) $\Delta Gain/Gain_0$, instead of $\Delta Gain$, was the consistent variable among tested devices. This response can be resulted from the ionic-liquid microcrystals being dissolved. This would lead to the destruction of the sensor network. To test this, the devices were exposed from the high water content experiments to DCP vapor and found a substantially attenuated response was obtained. This is consistent with a compromised sensor. Similarly, the response was attenuated when the device was exposed a mixed flow of high water content vapor and DCP vapor.

Other embodiments are within the scope of the following claims.

What is claimed is:

1. A system for detecting a stimulus comprising:
   a radio frequency device comprising a sensor element comprising an integrated circuit and a first resistive element, wherein the sensor element comprises a material responsive to an analyte and which is configured to elicit a response when a stimulus contacts or interacts with the radio frequency device; and
   a portable reader adapted to
   transmit radio frequency waves to the radio frequency device;
   receive a spectrum of radio frequency waves from the radio frequency device; and
   relate a characteristic of the spectrum to a concentration of the analyte,
   wherein the characteristic of the spectrum comprises a gain of the radio frequency device and/or a reflected attenuated signal of the radio frequency device.

2. The system of claim 1, wherein the sensor element comprises a second resistive element.

3. The system of claim 2, wherein the second resistive element is parallel to the integrated circuit.

4. The system of claim 1, wherein the sensor element comprises a second resistive element, wherein the second resistive element is in series with a circuitry of the integrated circuit.

5. The system of claim 1, wherein the sensor element comprises a capacitive element.

6. The system of claim 5, wherein the capacitive element is parallel to the integrated circuit.

7. The system of claim 1, wherein the material of the sensor element comprises a chemiresistive material.

8. The system of claim 1, wherein the sensor element is responsive to at least one of temperature, heat energy exposure, or radiation.

9. The system of claim 1, wherein the characteristic of the spectrum comprises the gain of the radio frequency device.

10. The system of claim 9, wherein the characteristic of the spectrum further comprises a resonant frequency of the radio frequency device.

11. The system of claim 1, wherein the characteristic of the spectrum comprises the reflected attenuated signal of the radio frequency device.

12. The system of claim 1, wherein the sensor element is wirelessly readable.

13. The system of claim 12, wherein the sensor element is also non-line of sight readable.

14. The system of claim 1, wherein the material of the sensor element includes a metal, an organic material, a dielectric material, a semiconductor material, a polymeric material, a biological material, a nanowire, a semiconducting nanoparticle, a carbon nanotube, a carbon nanotube network, a nanofiber, a carbon fiber, a carbon particle, carbon paste, conducting ink, or a combination thereof.

15. The system of claim 14, wherein the sensor element has a property that can change upon exposure to an environment including at least one of a change in capacitance, a change in resistance, a change in thickness, a change in viscoelasticity, or a combination thereof.

16. The system of claim 1, wherein the portable reader is configured to send an alert to a user when an analyte concentration detection threshold is reached.

17. The system of claim 16, wherein the portable reader is configured to send an email or text alert to the user when the analyte concentration detection threshold is exceeded.

18. The system of claim 1, wherein the portable reader is configured to monitor spatiotemporal changes in concentrations of chemical emissions from the sensor element and send an emergency alert to a user when a safe threshold is exceeded.

* * * * *